(12) United States Patent
Lipkens et al.

(10) Patent No.: US 9,228,183 B2
(45) Date of Patent: Jan. 5, 2016

(54) ACOUSTOPHORETIC SEPARATION TECHNOLOGY USING MULTI-DIMENSIONAL STANDING WAVES

(71) Applicant: FLODESIGN SONICS, INC., Wilbraham, MA (US)

(72) Inventors: Bart Lipkens, Hampden, MA (US); Jason Dionne, Simsbury, CT (US); Walter M. Presz, Jr., Wilbraham, MA (US); Thomas J. Kennedy, III, Wilbraham, MA (US)

(73) Assignee: FloDesign Sonics, Inc., Wilbraham, MA (US)

(*) Notice: Subject to any disclaimer, the term of this patent is extended or adjusted under 35 U.S.C. 154(b) by 0 days.

(21) Appl. No.: 14/557,040

(22) Filed: Dec. 1, 2014

(65) Prior Publication Data
US 2015/0176001 A1  Jun. 25, 2015

Related U.S. Application Data

(60) Division of application No. 14/026,413, filed on Sep. 13, 2013, which is a continuation-in-part of application No. 13/844,754, filed on Mar. 15, 2013.

(60) Provisional application No. 61/708,641, filed on Oct.
(Continued)

(51) Int. Cl.
| | |
|---|---|
| B01D 21/28 | (2006.01) |
| C12N 13/00 | (2006.01) |
| H01L 41/053 | (2006.01) |
| B01D 17/04 | (2006.01) |
| B06B 1/06 | (2006.01) |
| C12M 1/00 | (2006.01) |

(52) U.S. Cl.
CPC .............. *C12N 13/00* (2013.01); *B01D 17/044* (2013.01); *B01D 21/28* (2013.01); *B06B 1/0644* (2013.01); *H01L 41/053* (2013.01); *C12M 47/02* (2013.01)

(58) Field of Classification Search
CPC ................... B01D 29/115; B01D 2201/0415; B01D 2201/127; B01D 37/00; B01D 21/28
USPC ......... 210/748.01–748.05, 321.6–321.9, 542; 422/20, 292, 306; 209/155, 156; 436/177
See application file for complete search history.

(56) References Cited

U.S. PATENT DOCUMENTS 2,473,971 A * 6/1949 Ross .............................. 181/198
2,667,944 A   2/1954 Crites
(Continued)

FOREIGN PATENT DOCUMENTS

| DE | 30 27 433 A1 | 2/1982 |
|---|---|---|
| EP | 0 292 470 B1 | 11/1988 |

(Continued)

OTHER PUBLICATIONS

Wang et al. 'Retention and Viability Characteristics of Mammalian Cells in an Acoustically Driven Polymer Mesh' Biotechnol Prog. Jan.-Feb. 3004;20(1):384-7; p. 384, col. 1, para 2, para 1; Fig 1; p. 385, col. 2, para 2; p. 385, col. 1, para 1; p. 385, col. 1, para 2; p. 384, para 3; p. 384; col. 2, ast para; p. 385, col. 1 para 1.*

(Continued)

*Primary Examiner* — Walter D Griffin
*Assistant Examiner* — Cameron J Allen
(74) *Attorney, Agent, or Firm* — Richard M. Klein; Fay Sharpe LLP

(57) ABSTRACT

A system having improved trapping force for acoustophoresis is described where the trapping force is improved by manipulation of the frequency of the ultrasonic transducer. The transducer includes a ceramic crystal. The crystal may be directly exposed to fluid flow. The crystal may be air backed, resulting in a higher Q factor.

54 Claims, 33 Drawing Sheets

Related U.S. Application Data 2, 2012, provisional application No. 61/611,159, filed on Mar. 15, 2012, provisional application No. 61/611,240, filed on Mar. 15, 2012, provisional application No. 61/754,792, filed on Jan. 21, 2013.

(56) References Cited

U.S. PATENT DOCUMENTS

| | | | |
|---|---|---|---|
| 3,555,311 A | 1/1971 | Weber | |
| 4,055,491 A | 10/1977 | Porath-Furedi | |
| 4,158,629 A | 6/1979 | Sawyer | |
| 4,165,273 A | 8/1979 | Azarov et al. | |
| 4,173,725 A | 11/1979 | Asai et al. | |
| 4,204,096 A | 5/1980 | Barcus et al. | |
| 4,398,325 A | 8/1983 | Piaget et al. | |
| 4,666,595 A | 5/1987 | Graham | |
| 4,699,588 A | 10/1987 | Zinn et al. | |
| 4,743,361 A | 5/1988 | Schram | |
| 4,759,775 A | 7/1988 | Peterson et al. | |
| 4,983,189 A | 1/1991 | Peterson et al. | |
| 5,085,783 A | 2/1992 | Feke et al. | |
| 5,225,089 A | 7/1993 | Benes et al. | |
| 5,371,429 A | 12/1994 | Manna | |
| 5,395,592 A | 3/1995 | Bolleman et al. | |
| 5,431,817 A | 7/1995 | Braatz et al. | |
| 5,443,985 A | 8/1995 | Lu et al. | |
| 5,452,267 A | 9/1995 | Spevak | |
| 5,484,537 A | 1/1996 | Whitworth | |
| 5,527,460 A | 6/1996 | Trampler et al. | |
| 5,560,362 A | 10/1996 | Sliwa, Jr. et al. | |
| 5,594,165 A | 1/1997 | Madanshetty | |
| 5,604,301 A | 2/1997 | Mountford et al. | |
| 5,626,767 A | 5/1997 | Trampler et al. | |
| 5,688,405 A | 11/1997 | Dickinson et al. | |
| 5,711,888 A * | 1/1998 | Trampler et al. | 210/748.05 |
| 5,831,166 A | 11/1998 | Kozuka et al. | |
| 5,902,489 A | 5/1999 | Yasuda et al. | |
| 5,912,182 A | 6/1999 | Coakley et al. | |
| 5,951,456 A | 9/1999 | Scott | |
| 6,090,295 A | 7/2000 | Raghavarao et al. | |
| 6,166,231 A | 12/2000 | Hoeksema | |
| 6,205,848 B1 | 3/2001 | Faber et al. | |
| 6,216,538 B1 | 4/2001 | Yasuda et al. | |
| 6,332,541 B1 | 12/2001 | Coakley et al. | |
| 6,391,653 B1 | 5/2002 | Letcher et al. | |
| 6,487,095 B1 | 11/2002 | Malik et al. | |
| 6,592,821 B1 | 7/2003 | Wada et al. | |
| 6,649,069 B2 | 11/2003 | DeAngelis | |
| 6,763,722 B2 | 7/2004 | Fjield et al. | |
| 6,881,314 B1 | 4/2005 | Wang et al. | |
| 6,929,750 B2 | 8/2005 | Laurell et al. | |
| 6,936,151 B1 | 8/2005 | Lock et al. | |
| 7,010,979 B2 | 3/2006 | Scott | |
| 7,061,163 B2 | 6/2006 | Nagahara et al. | |
| 7,081,192 B1 | 7/2006 | Wang et al. | |
| 7,093,482 B2 | 8/2006 | Berndt | |
| 7,108,137 B2 | 9/2006 | Lal et al. | |
| 7,150,779 B2 | 12/2006 | Meegan, Jr. | |
| 7,186,502 B2 | 3/2007 | Vesey | |
| 7,191,787 B1 | 3/2007 | Redeker et al. | |
| 7,322,431 B2 * | 1/2008 | Ratcliff | 175/206 |
| 7,331,233 B2 | 2/2008 | Scott | |
| 7,340,957 B2 | 3/2008 | Kaduchak et al. | |
| 7,373,805 B2 | 5/2008 | Hawkes et al. | |
| 7,541,166 B2 | 6/2009 | Belgrader et al. | |
| 7,601,267 B2 | 10/2009 | Haake et al. | |
| 7,673,516 B2 | 3/2010 | Janssen et al. | |
| 7,837,040 B2 | 11/2010 | Ward et al. | |
| 7,846,382 B2 | 12/2010 | Strand et al. | |
| 7,968,049 B2 | 6/2011 | Takahashi et al. | |
| 8,080,202 B2 | 12/2011 | Takahashi et al. | |
| 8,256,076 B1 | 9/2012 | Feller | |
| 8,266,950 B2 | 9/2012 | Kaduchak et al. | |
| 8,273,253 B2 | 9/2012 | Curran | |
| 8,273,302 B2 | 9/2012 | Takahashi et al. | |
| 8,309,408 B2 | 11/2012 | Ward et al. | |
| 8,319,398 B2 | 11/2012 | Vivek et al. | |
| 8,334,133 B2 | 12/2012 | Fedorov et al. | |
| 8,387,803 B2 | 3/2013 | Thorslund et al. | |
| 8,679,338 B2 | 3/2014 | Rietman et al. | |
| 8,714,360 B2 * | 5/2014 | Swayze et al. | 209/143 |
| 2002/0038662 A1 * | 4/2002 | Schuler et al. | 134/1.3 |
| 2002/0134734 A1 | 9/2002 | Campbell et al. | |
| 2003/0195496 A1 | 10/2003 | Maguire | |
| 2003/0209500 A1 | 11/2003 | Kock et al. | |
| 2003/0230535 A1 | 12/2003 | Affeld et al. | |
| 2004/0016699 A1 | 1/2004 | Bayevsky | |
| 2005/0145567 A1 * | 7/2005 | Quintel et al. | 210/636 |
| 2005/0196725 A1 | 9/2005 | Fu | |
| 2006/0037915 A1 | 2/2006 | Strand et al. | |
| 2007/0272618 A1 | 11/2007 | Gou et al. | |
| 2007/0284299 A1 | 12/2007 | Xu et al. | |
| 2008/0217259 A1 | 9/2008 | Siversson | |
| 2009/0029870 A1 | 1/2009 | Ward et al. | |
| 2009/0045107 A1 | 2/2009 | Ward et al. | |
| 2009/0053686 A1 | 2/2009 | Ward et al. | |
| 2009/0098027 A1 | 4/2009 | Tabata et al. | |
| 2009/0178716 A1 | 7/2009 | Kaduchak et al. | |
| 2009/0194420 A1 | 8/2009 | Mariella, Jr. et al. | |
| 2009/0226994 A1 | 9/2009 | Lemor et al. | |
| 2009/0295505 A1 | 12/2009 | Mohammadi et al. | |
| 2010/0000945 A1 | 1/2010 | Gavalas | |
| 2010/0078384 A1 | 4/2010 | Yang | |
| 2010/0124142 A1 | 5/2010 | Laugharn et al. | |
| 2010/0192693 A1 | 8/2010 | Mudge et al. | |
| 2010/0193407 A1 | 8/2010 | Steinberg et al. | |
| 2010/0206818 A1 * | 8/2010 | Leong et al. | 210/748.05 |
| 2010/0255573 A1 | 10/2010 | Bond et al. | |
| 2010/0261918 A1 | 10/2010 | Chianelli et al. | |
| 2010/0317088 A1 | 12/2010 | Radaelli et al. | |
| 2010/0323342 A1 | 12/2010 | Gonzalez Gomez et al. | |
| 2010/0330633 A1 | 12/2010 | Walther et al. | |
| 2011/0003350 A1 | 1/2011 | Schafran et al. | |
| 2011/0024335 A1 | 2/2011 | Ward et al. | |
| 2011/0092726 A1 | 4/2011 | Clarke | |
| 2011/0095225 A1 | 4/2011 | Eckelberry et al. | |
| 2011/0123392 A1 | 5/2011 | Dionne et al. | |
| 2011/0154890 A1 | 6/2011 | Holm et al. | |
| 2011/0166551 A1 | 7/2011 | Schafer | |
| 2011/0262990 A1 | 10/2011 | Wang et al. | |
| 2011/0278218 A1 | 11/2011 | Dionne et al. | |
| 2011/0281319 A1 | 11/2011 | Swayze et al. | |
| 2011/0309020 A1 | 12/2011 | Rietman et al. | |
| 2012/0088295 A1 | 4/2012 | Yasuda et al. | |
| 2012/0163126 A1 | 6/2012 | Campbell et al. | |
| 2012/0328477 A1 | 12/2012 | Dionne et al. | |
| 2012/0329122 A1 | 12/2012 | Lipkens et al. | |
| 2013/0277316 A1 | 10/2013 | Dutra et al. | |
| 2013/0284271 A1 | 10/2013 | Lipkens et al. | |
| 2014/0011240 A1 | 1/2014 | Lipkens et al. | |

FOREIGN PATENT DOCUMENTS

| | | |
|---|---|---|
| EP | 1 254 669 B1 | 11/2002 |
| GB | 2 420 510 A | 5/2006 |
| WO | WO 87/07178 A1 | 12/1987 |
| WO | WO 00/41794 | 7/2000 |
| WO | WO 02/072234 A1 | 9/2002 |
| WO | WO 2009/111276 A1 | 9/2009 |
| WO | WO 2009/144709 A1 | 12/2009 |
| WO | WO 2010/024753 A1 | 4/2010 |
| WO | WO 2011/023949 A2 | 3/2011 |
| WO | WO 2011/027146 A2 | 3/2011 |
| WO | WO 2011/161463 A2 | 12/2011 |

OTHER PUBLICATIONS

International Search Report dated Feb. 18, 2014 in corresponding PCT Application No. PCT/US2013/059640.
Alvarez et al.; Shock Waves, vol. 17, No. 6, pp. 441-447, 2008.
Benes et al.; Ultrasonic Separation of Suspended Particles, 2001 IEEE Ultrasonics Symposium; Oct. 7-10, 2001; pp. 649-659; Atlanta, Georgia.

(56) References Cited

OTHER PUBLICATIONS

Castro; Tunable gap and quantum quench dynamics in bilayer graphene; Jul. 13, 2010; Mathematica Summer School.
Cravotto et al.; Ultrasonics Sonochemistry, vol. 15, No. 5, pp. 898-902, 2008.
Garcia-Lopez, et al; Enhanced Acoustic Separation of Oil-Water Emulsion in Resonant Cavities. The Open Acoustics Journal. 2008, vol. 1, pp. 66-71.
Hill et al.; Ultrasonic Particle Manipulation; Microfluidic Technologies for Miniaturized Analysis Systems, Jan. 2007, pp. 359-378.
Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.
Latt et al.; Ultrasound-membrane hybrid processes for enhancement of filtration properties; Ultrasonics sonochemistry 13.4 (2006): 321-328.
Lipkens et al.; Frequency sweeping and fluid flow effects on particle trajectories in ultrasonic standing waves; Acoustics 08, Paris, Jun. 29-Jul. 4, 2008.
Lipkens et al.; Prediction and measurement of particle velocities in ultrasonic standing waves; J. Acoust. Soc. Am., 124 No. 4, pp. 2492 (A) 2008.
Lipkens et al.; Separation of micron-sized particles in macro-scale cavities by ultrasonic standing waves; Presented at the International Congress on Ultrasonics, Santiago; Jan. 11-17, 2009.
Lipkens et al.; The effect of frequency sweeping and fluid flow on particle trajectories in ultrasonic standing waves; IEEE Sensors Journal, vol. 8, No. 6, pp. 667-677, 2008.
Lipkens et al., Macro-scale acoustophoretic separation of lipid particles from red blood cells, The Journal of the Acoustical Society of America, vol. 133, Jun. 2, 2013, p. 045017, XP055162509, New York, NY.
Meribout et a.; An Industrial-Prototype Acoustic Array for Real-Time Emulsion Layer Detection in Oil Storage Tanks; IEEE Sensors Journal, vol. 9, No. 12, Dec. 2009.
Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.
Pangu et al.; Droplet transport and coalescence kinetics in emulsions subjected to acoustic fields; Ultrasonics 46, pp. 289-302 (2007).
Ponomarenko et al.; Density of states and zero Landau level probed through capacitance of graphene; Nature Nanotechnology Letters, Jul. 5, 2009; DOI: 10.1038/NNANO.2009.177.
Seymour et al, J. Chem. Edu., 1990, 67(9), p. 763, published Sep. 1990.
Annex to Form PCT/ISA/206—Communication Relating to the Results of the Partial International Search Report, dated Jul. 18, 2013.
European Search Report of European Application No. 11769474.5 Dated Oct. 10, 2012.
International Search Report and Written Opinion dated Dec. 20, 2011, for corresponding PCT application No. PCT/US2011/032181.
International Search Report and Written Opinion dated Feb. 27, 2012, for PCT application No. PCT/US2011/040787.
International Search Report and Written Opinion of International Application No. PCT/US2013/037404 Dated Jun. 21, 2013.
International Search Report and Written Opinion of International Application No. PCT/US2013/050729 Dated Sep. 25, 2013.
International Search Report for corresponding PCT Application Serial No. PCT/US2014/015382 dated May 6, 2014.
Phys. Org. "Engineers develop revolutionary nanotech water desalination membrane." Nov. 6, 2006. http://phys.org/news82047372.html.
"Proceedings of the Acoustics 2012 Nantes Conference," Apr. 23-27, 2012, Nantes, France, pp. 278-282.
Sony New Release: <http://www.sony.net/SonyInfo/News/Press/201010/10-137E/index.html>.

* cited by examiner

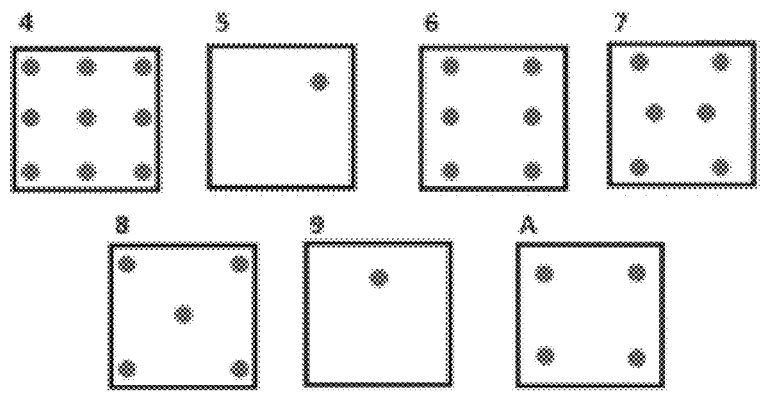
FIGURE 21A
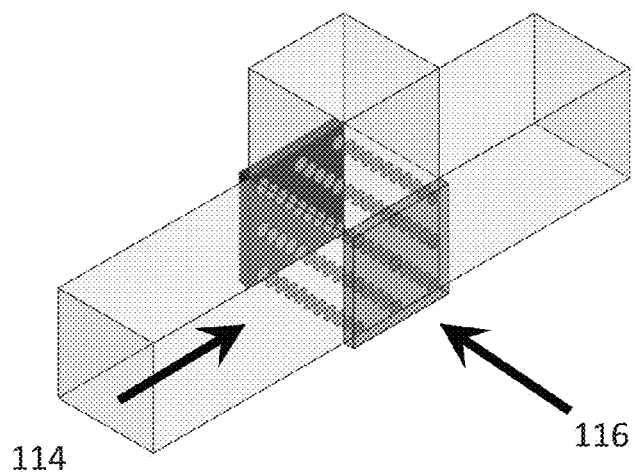
FIGURE 21B
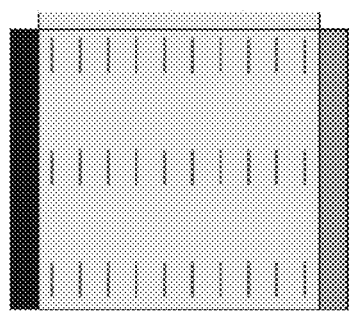 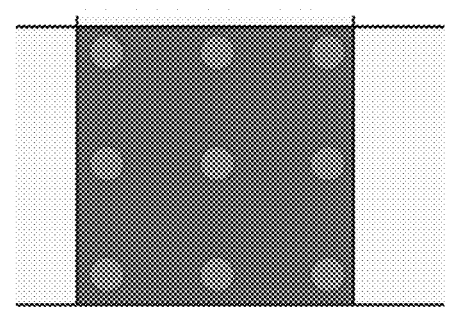
FIGURE 21C　　　　　　　　FIGURE 21D

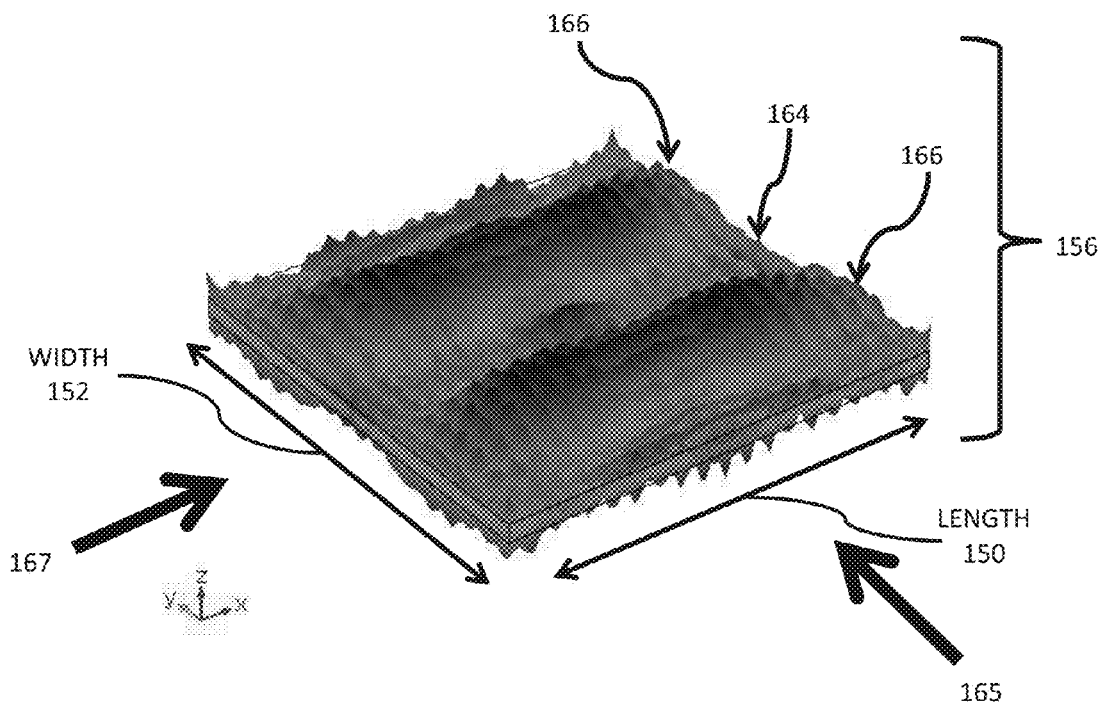
FIGURE 36A
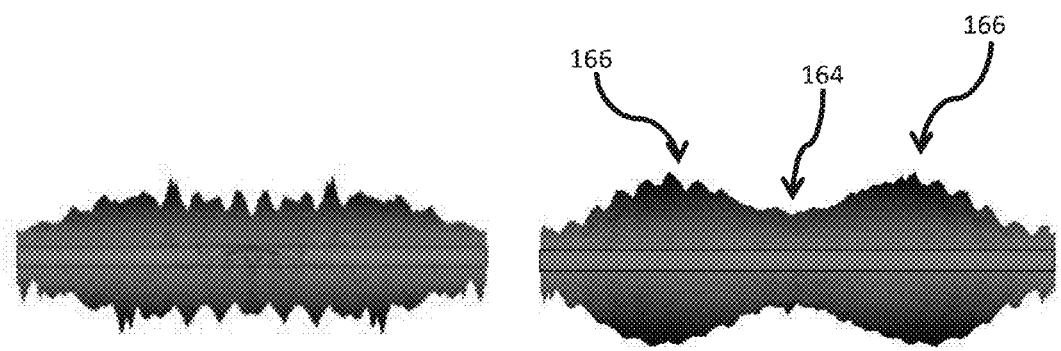
FIGURE 36B
FIGURE 36C

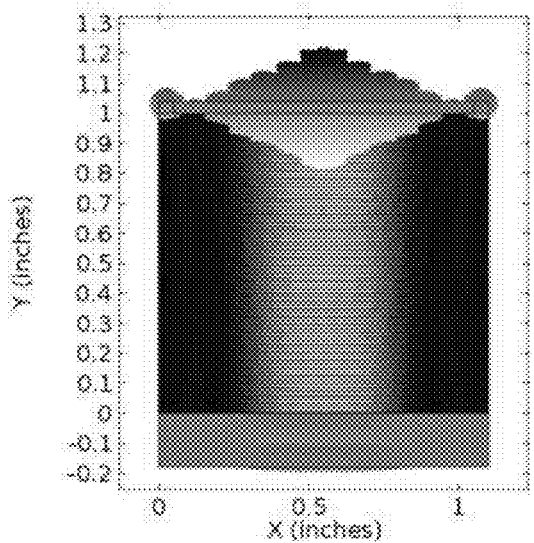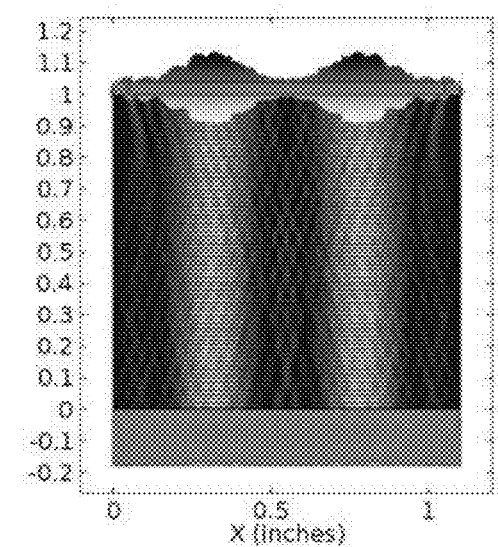
FIGURE 39A  FIGURE 39B
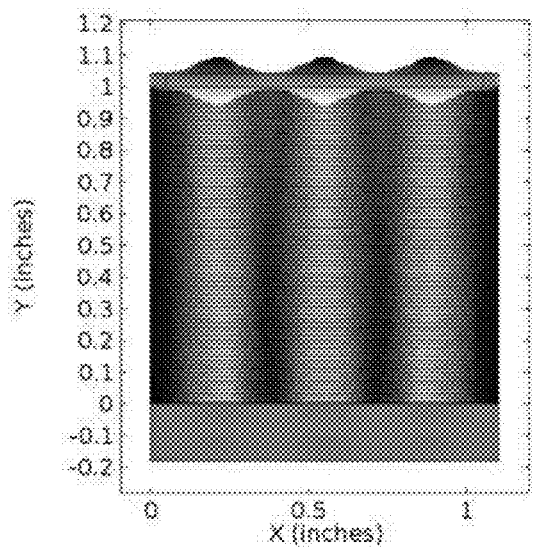
FIGURE 39C

ACOUSTOPHORETIC SEPARATION TECHNOLOGY USING MULTI-DIMENSIONAL STANDING WAVES

This application is a divisional of U.S. patent application Ser. No. 14/026,413, filed on Sep. 13, 2013, which claims the benefit of U.S. Provisional Patent Application Ser. No. 61/708,641, filed on Oct. 2, 2012. U.S. patent application Ser. No. 14/026,413 is also a continuation-in-part of U.S. Ser. No. 13/844,754, filed Mar. 15, 2013, which claimed the benefit of U.S. Provisional Patent Application Ser. No. 61/611,159, filed Mar. 15, 2012, and of U.S. Provisional Patent Application Ser. No. 61/611,240, also filed Mar. 15, 2012, and of U.S. Provisional Patent Application Ser. No. 61/754,792, filed Jan. 21, 2013. These applications are incorporated herein by reference in their entireties.

BACKGROUND

Acoustophoresis is the separation of particles using high intensity sound waves. It has long been known that high intensity standing waves of sound can exert forces on particles. A standing wave has a pressure profile which appears to "stand" still in time. The pressure profile in a standing wave varies from areas of high pressure (nodes) to areas of low pressure (anti-nodes). Standing waves are produced in acoustic resonators. Common examples of acoustic resonators include many musical wind instruments such as organ pipes, flutes, clarinets, and horns.

Efficient separation technologies for multi-component liquid streams that eliminate any waste and reduce the required energy, thereby promoting a sustainable environment, are needed.

BRIEF DESCRIPTION

The present disclosure relates to systems and devices for acoustophoresis on preferably a large scale. The devices use one or more unique ultrasonic transducers as described herein, or an array of such transducers. The transducer is driven at frequencies that produce multi-dimensional standing waves.

In some embodiments, an apparatus is disclosed that includes a flow chamber with at least one inlet and at least one outlet through which a mixture of a host fluid and at least one of a second fluid and a particulate is flowed. At least one ultrasonic transducer is embedded in a wall of said flow chamber or located outside the flow chamber wall and is driven by an oscillating, periodic, modulated, or pulsed voltage signal of ultrasonic frequencies which drives the transducer in a higher order mode of vibration to create multi-dimensional standing waves in the flow channel. The transducer includes a ceramic crystal or other piezoelectric material having certain vibration characteristics. A solid or flexible reflector is located on the wall on the opposite side of the flow chamber from the transducer. The apparatus may further include an apparatus inlet that feeds into an annular plenum, as well as two outlets located on different walls of the apparatus.

In other embodiments, a method of separating a host fluid from at least one of a second fluid and/or a particulate is disclosed. The method comprises flowing the host fluid into a flow chamber having a resonator and a collection pocket or port and driving a transducer with an oscillating, periodic, modulated, or pulsed voltage signal to create standing waves of a multi-dimensional nature with the resonator and collect the at least one of the second fluid and/or particulate in the collection pocket.

In yet other embodiments, an apparatus comprises a flow chamber with at least one inlet and at least one outlet through which a mixture of a host fluid and at least one of a second fluid and a particulate is flowed. A plurality of ultrasonic transducers are embedded in a wall of said flow chamber or located outside the flow chamber wall. The transducers each include a ceramic crystal or other piezoelectric material driven by an oscillating, periodic, modulated, or pulsed voltage signal of ultrasonic frequencies which drives the transducers in a higher order mode of vibration to create multi-dimensional standing waves in the flow channel. A solid or flexible reflector is located on the wall on the opposite side of the flow chamber from the transducers. The apparatus may further include an apparatus inlet that feeds into an annular plenum, as well as two outlets located on different walls of the apparatus.

These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

FIG. 9A shows the axial force for a single standing wave. The text at the top of the scale on the right is "$\times 10^{-11}$". FIG. 9B shows the lateral force for a single standing wave. The text at the top of the scale on the right is "$\times 10^{-13}$". FIG. 9C shows the axial force with a multi-mode excitation. The text at the top of the scale on the right is "×10⁻¹⁰". FIG. 9D shows the lateral force with a multi-mode excitation. The text at the top of the scale on the right is "×10⁻¹¹". For all figures, the horizontal axis is the location along the X-axis of FIG. 8 within the chamber, in inches, and the vertical axis is the location along the Y-axis of FIG. 8 within the chamber, in inches. The scale on the right of each figure is in Newtons.

In FIG. 13, the scale on the right is in Pascals (Pa).

Figure 11:
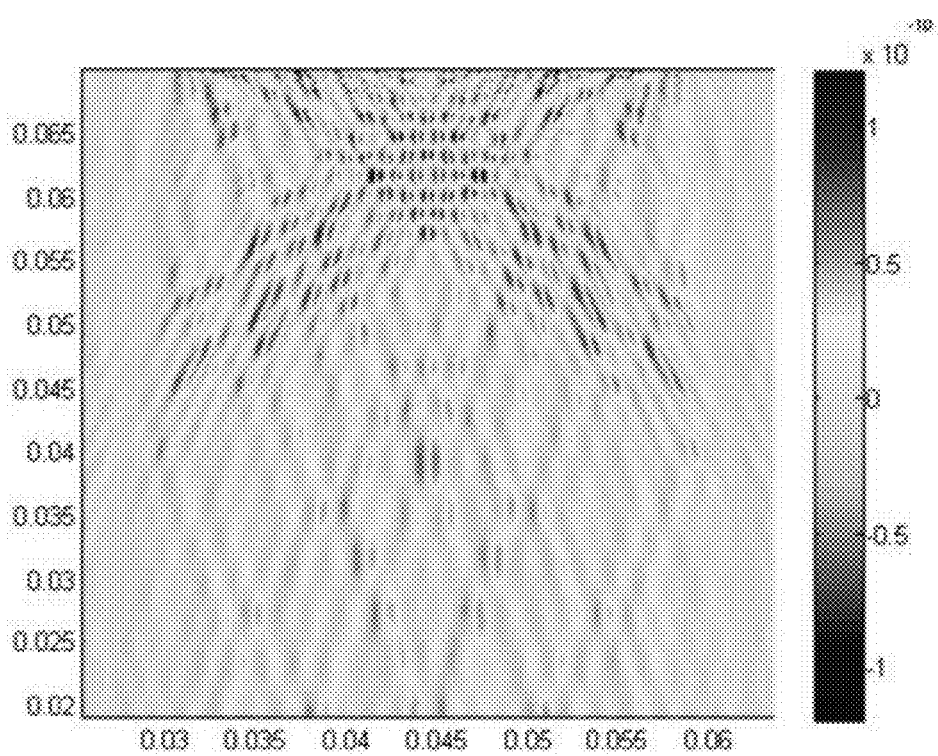
FIGS. 11-17 are additional simulations of the forces on a particle in an acoustophoretic separator. The horizontal axis is the location along the X-axis of FIG. 8 within the chamber, in inches, and the vertical axis is the location along the Y-axis of FIG. 8 within the chamber, in inches. The scale on the right is in Newtons (N) for all figures except FIG. 13.

The text at the top of the scale on the right in FIG. 11 is "×10⁻¹⁰".

Figure 12:
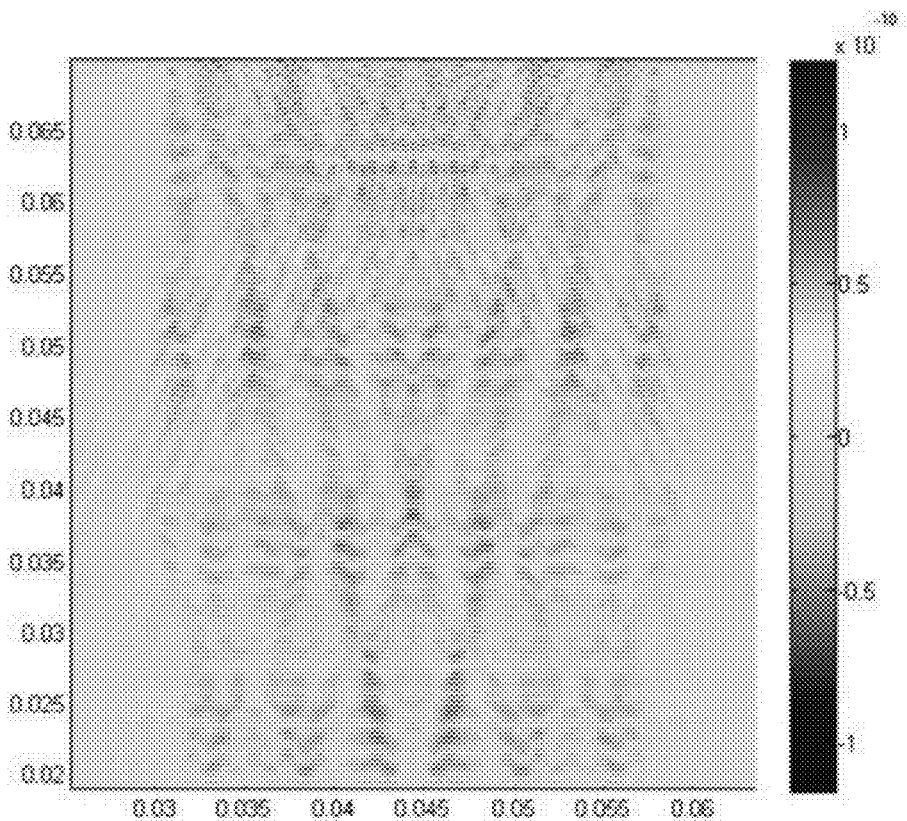

The text at the top of the scale on the right in FIG. 12 is "×10⁻¹⁰".

Figure 13:
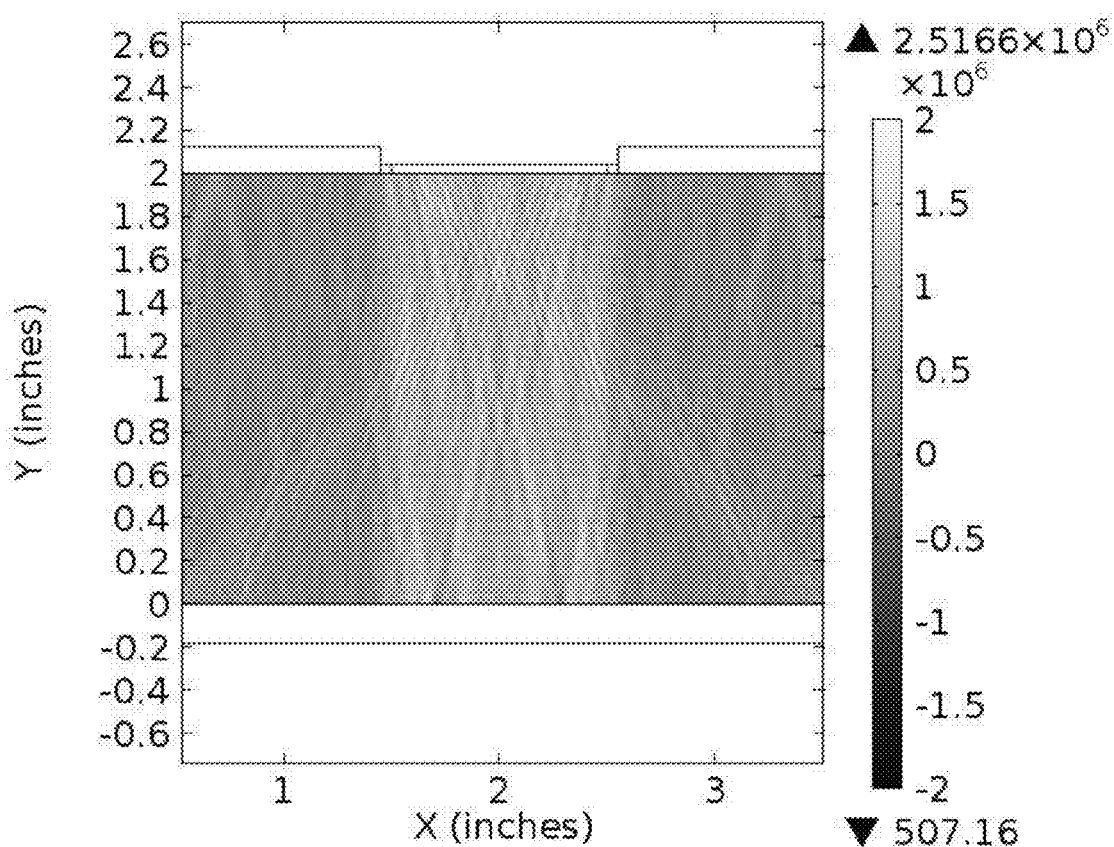

The text at the top of the scale on the right in FIG. 13 is "×10⁶". The text at the top by the upward-pointing triangle reads "2.5166×10⁶". The text at the bottom by the downward-pointing triangle reads "507.16". These two triangles show the maximum and minimum values depicted in this figure.

Figure 14:
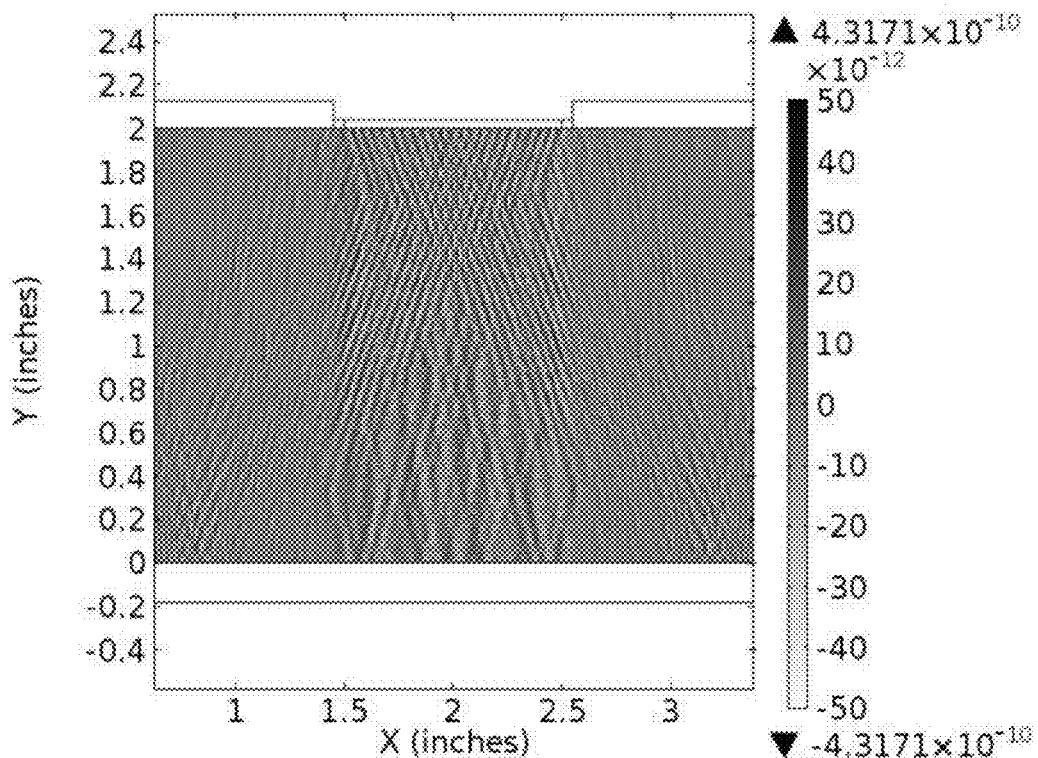

The text at the top of the scale on the right in FIG. 14 is "×10⁻¹²". The text at the top by the upward-pointing triangle reads "4.3171×10⁻¹⁰". The text at the bottom by the downward-pointing triangle reads "−4.3171×10⁻¹⁰". These two triangles show the maximum and minimum values depicted in this figure.

Figure 15:
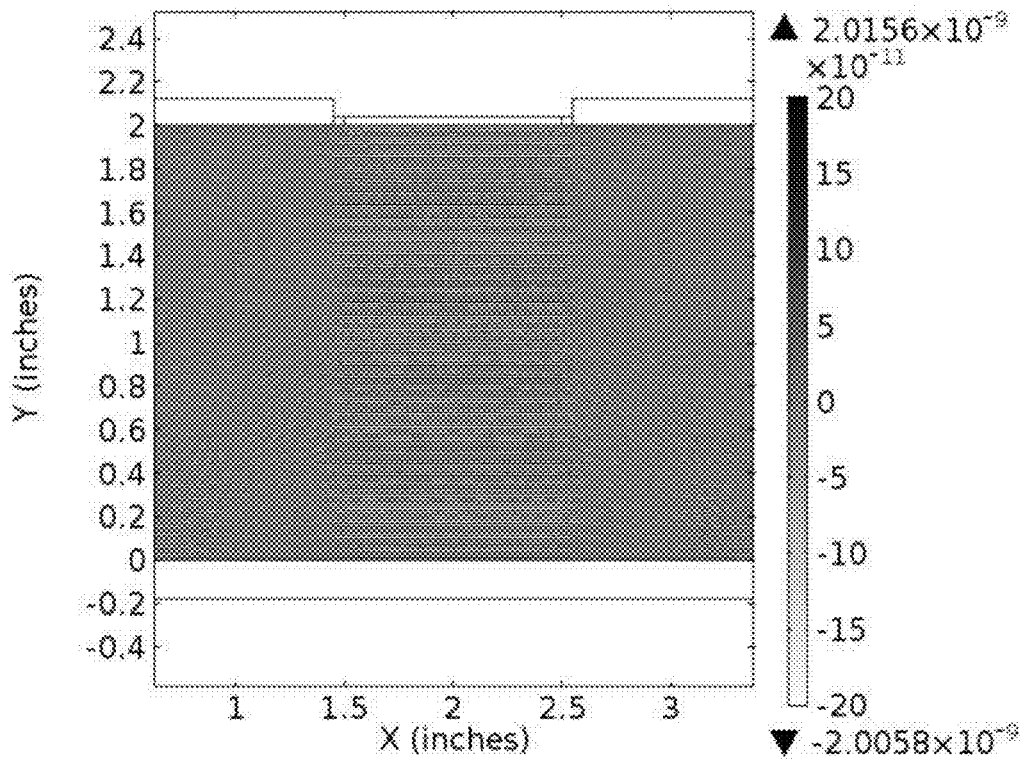

The text at the top of the scale on the right in FIG. 15 is "×10⁻¹¹". The text at the top by the upward-pointing triangle reads "2.0156×10⁻⁹". The text at the bottom by the downward-pointing triangle reads "−2.0058×10⁻⁹". These two triangles show the maximum and minimum values depicted in this figure.

Figure 16:
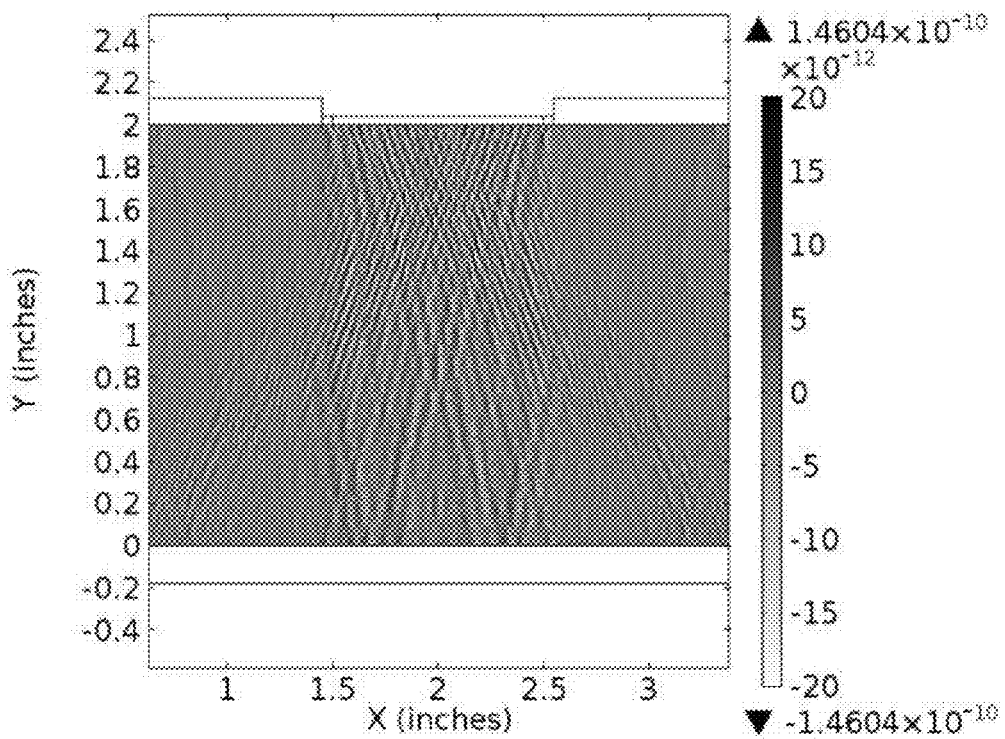

The text at the top of the scale on the right in FIG. 16 is "×10⁻¹²". The text at the top by the upward-pointing triangle reads "1.4606×10⁻¹⁰". The text at the bottom by the downward-pointing triangle reads "−1.4604×10⁻¹⁰". These two triangles show the maximum and minimum values depicted in this figure.

Figure 17:
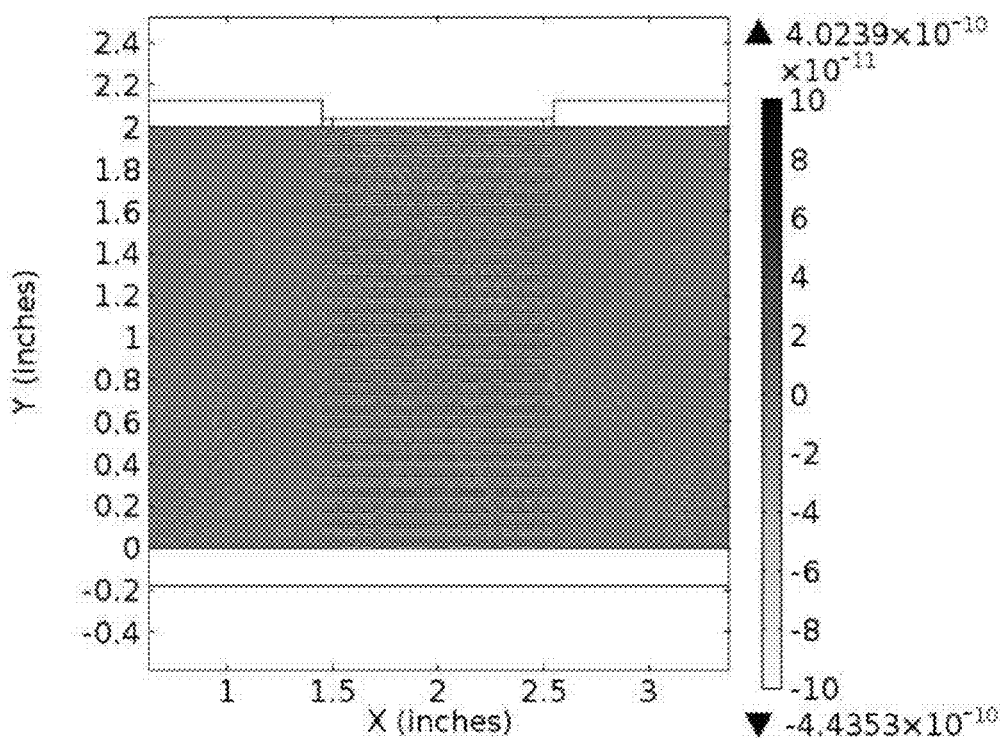

The text at the top of the scale on the right in FIG. 17 is "×10⁻¹¹". The text at the top by the upward-pointing triangle reads "4.0239×10⁻¹⁰". The text at the bottom by the downward-pointing triangle reads "−4.4353×10⁻¹⁰". These two triangles show the maximum and minimum values depicted in this figure.

Figure 18:
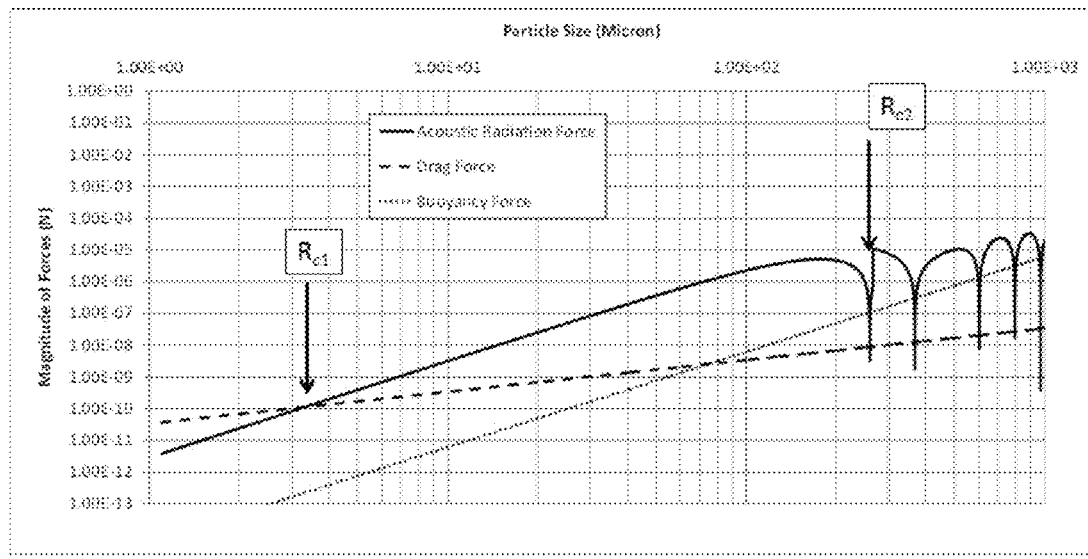

FIG. 18 is a graph showing the relationship of the acoustic radiation force, buoyancy force, and Stokes' drag force to particle size. The horizontal axis is in microns (μm) and the vertical axis is in Newtons (N).

Figure 19:
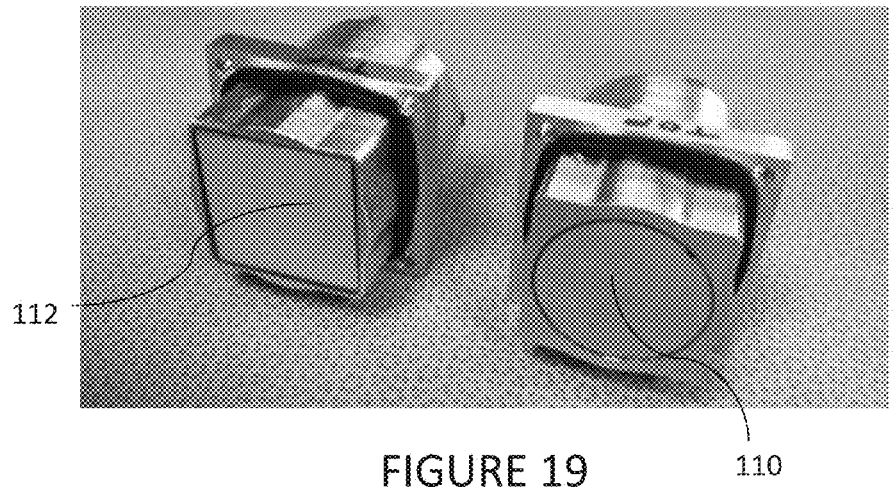

FIG. 19 is a photo of a square transducer and a circular transducer for use in an acoustophoretic separator.

Figure 20:
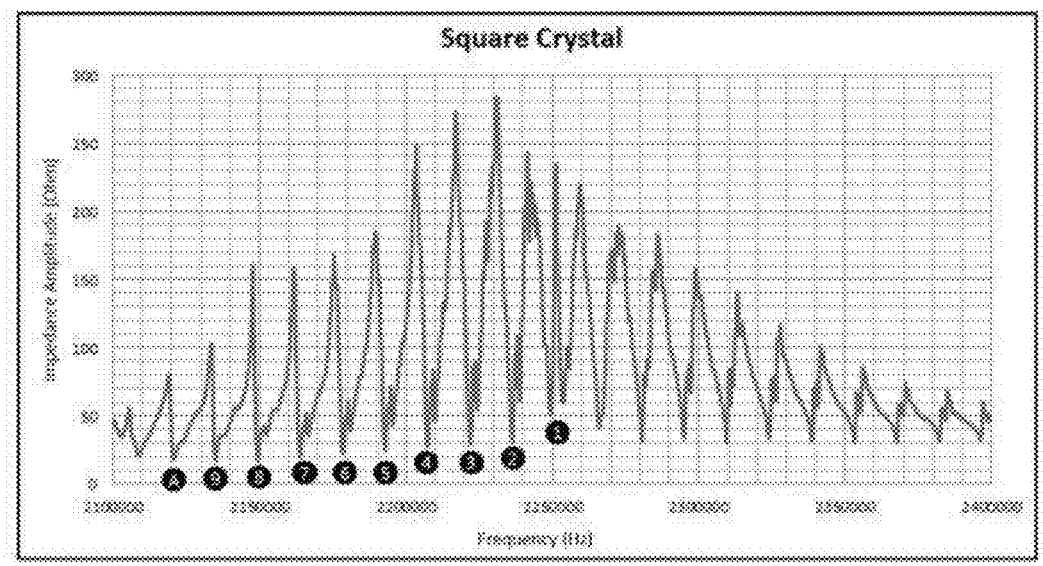

FIG. 20 is a graph of electrical impedance amplitude versus frequency for a square transducer driven at different frequencies.

FIG. 21A illustrates the trapping line configurations for seven of the peak amplitudes of FIG. 20 from the direction orthogonal to fluid flow.

FIG. 21B is a perspective view illustrating the separator. The fluid flow direction and the trapping lines are shown.

FIG. 21C is a view from the fluid inlet along the fluid flow direction (arrow 114) of FIG. 21B, showing the trapping nodes of the standing wave where particles would be captured.

FIG. 21D is a view taken through the transducers face at the trapping line configurations, along arrow 116 as shown in FIG. 21B.

Figure 22:
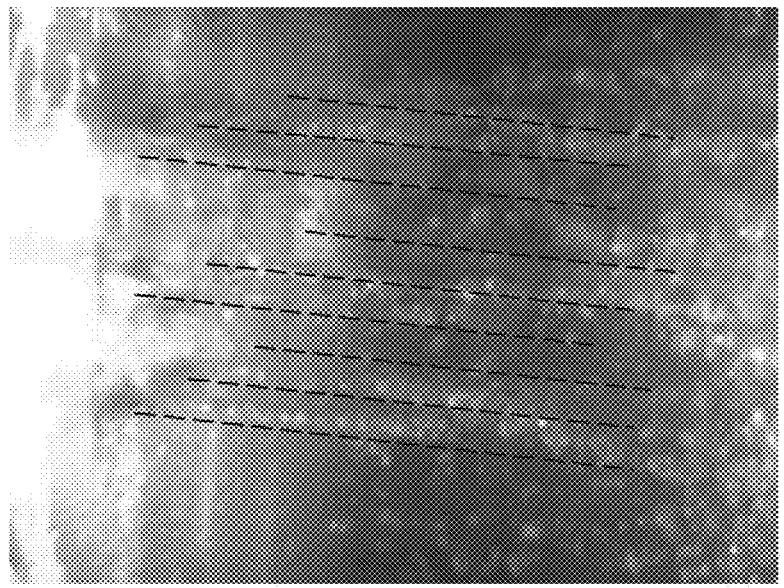

FIG. 22 is a photo of the nine-trapping-line configuration of a standing wave created by the multi-modal displacement of the transducer for an oil-water emulsion.

Figure 23:
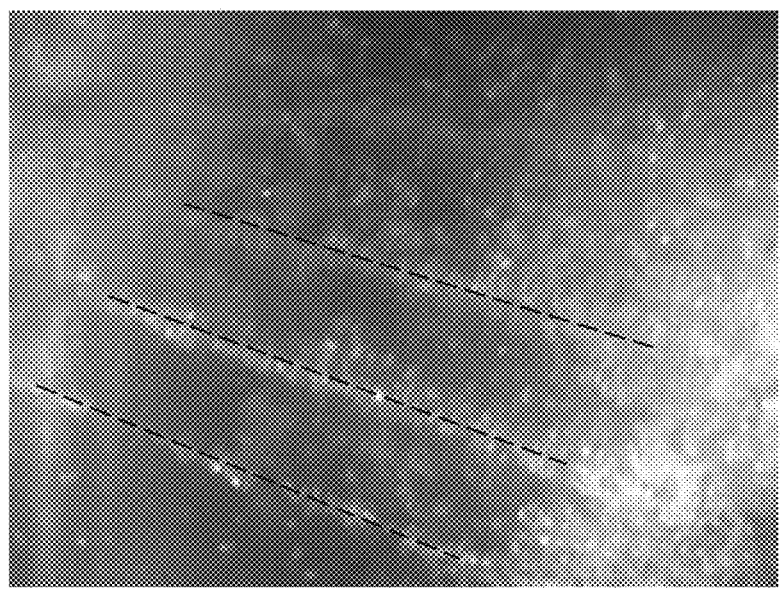

FIG. 23 is a zoom-in photo of FIG. 22 showing the upper three trapping lines of the nine-trapping-line configuration.

Figure 24:
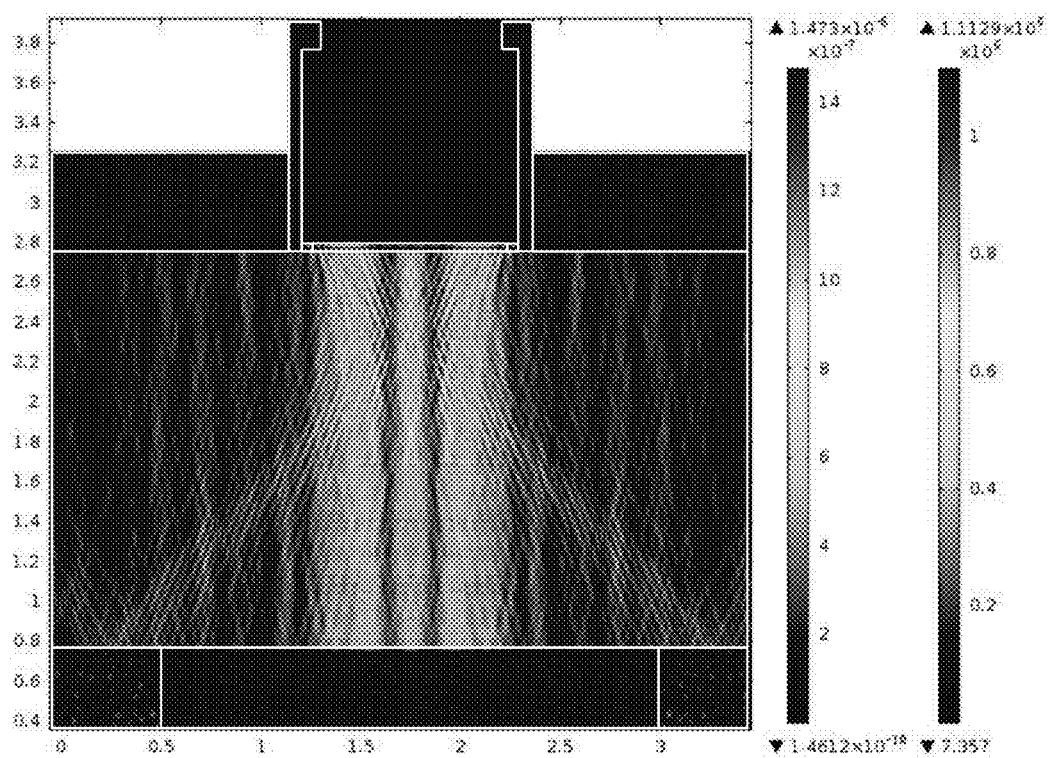

FIG. 24 is a computer simulation of the acoustic pressure amplitude (right-hand scale in Pa) and transducer out of plane displacement (left-hand scale in meters). The text at the top of the left-hand scale reads "×10⁻⁷". The text at the top of the left-hand scale by the upward-pointing triangle reads "1.473× 10⁻⁶". The text at the bottom of the left-hand scale by the downward-pointing triangle reads "1.4612×10⁻¹⁰". The text at the top of the right-hand scale reads "×10⁶". The text at the top of the right-hand scale by the upward-pointing triangle reads "1.1129×10⁶". The text at the bottom of the right-hand scale by the downward-pointing triangle reads "7.357". The triangles show the maximum and minimum values depicted in this figure for the given scale. The horizontal axis is the location within the chamber along the X-axis in FIG. 8, in inches, and the vertical axis is the location within the chamber along the Y-axis in FIG. 8, in inches.

Figure 25:
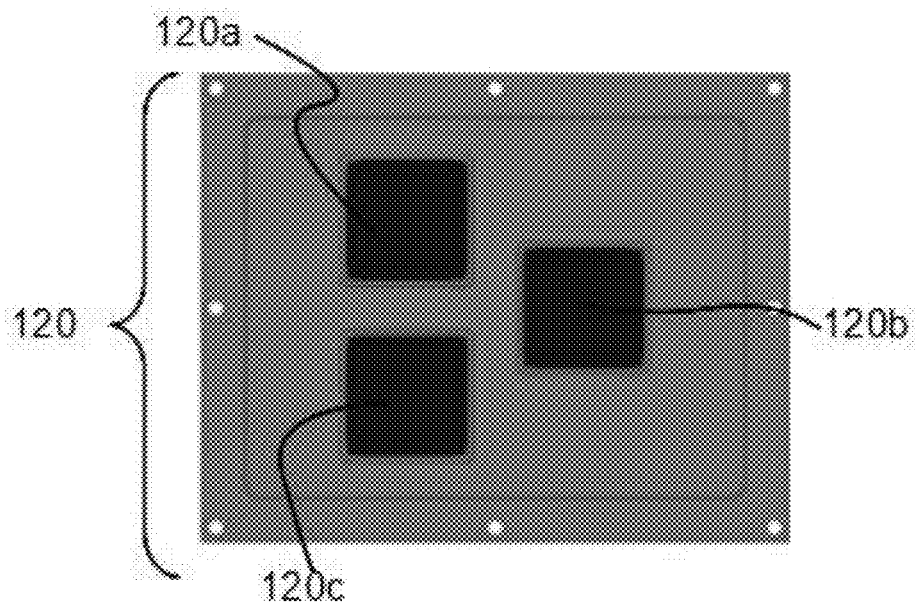
Figure 26:
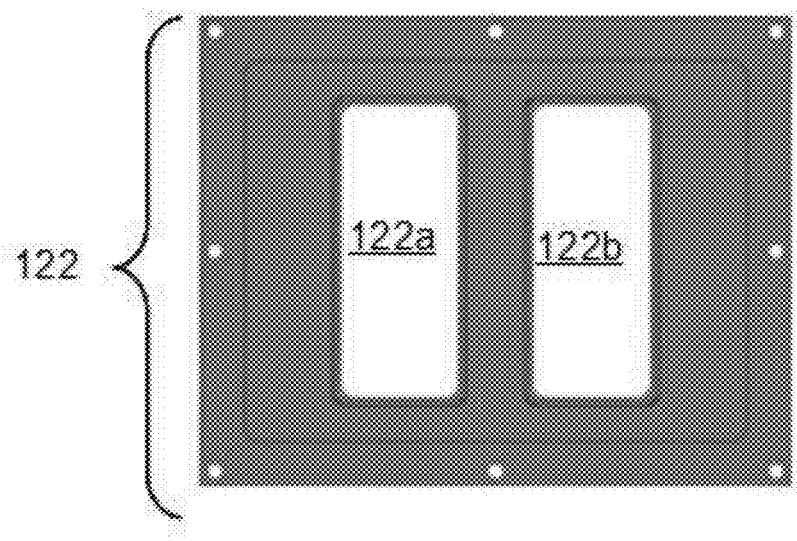

FIG. 25 and FIG. 26 show transducer array configurations.

Figure 27A:
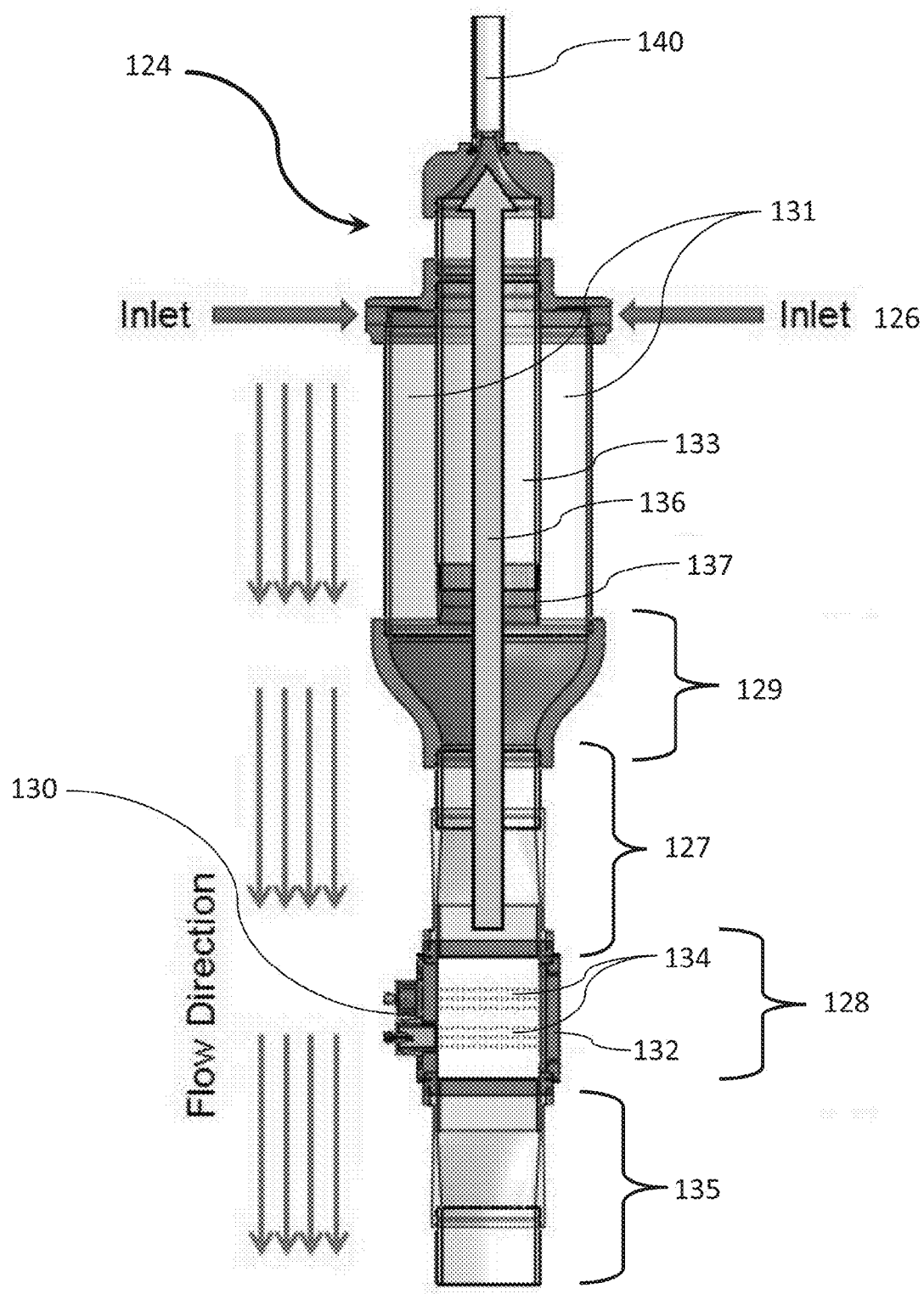

FIG. 27A shows an acoustophoretic separator for separating buoyant materials for use with the transducers of FIGS. 23 and 24.

Figure 27B:
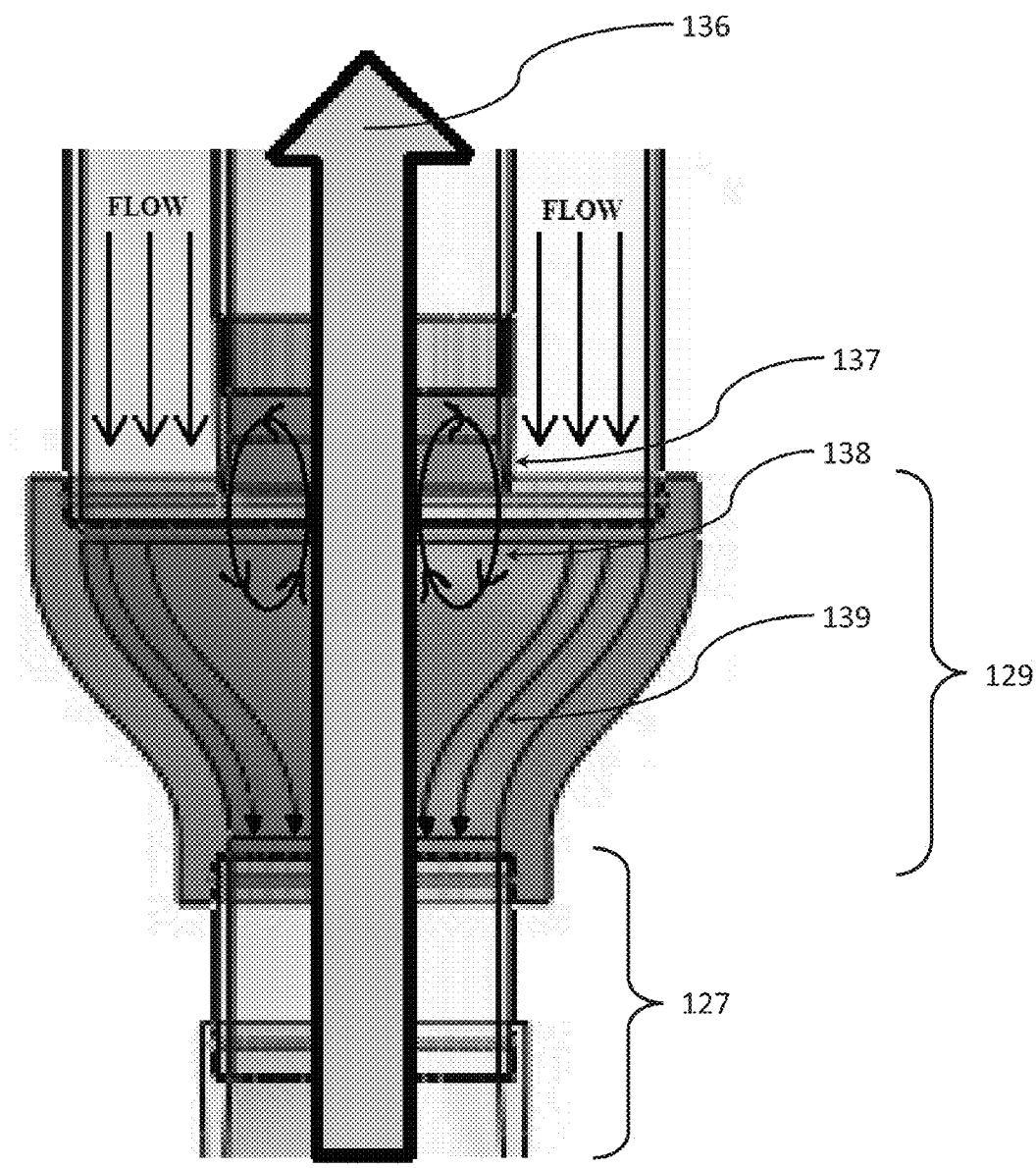

FIG. 27B is a magnified view of fluid flow near the intersection of the contoured nozzle wall 129 and the collection duct 137.

Figure 28:
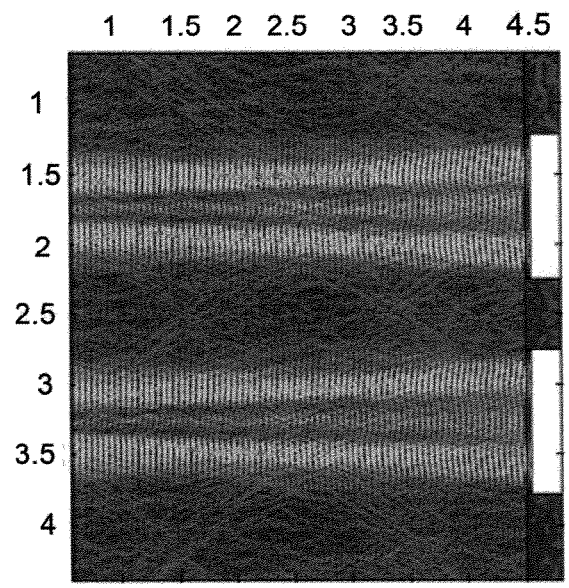

FIG. 28 is a computer simulation of the acoustic pressure amplitude of the ultrasonic waves generated by an array of transducers.

Figure 29:

FIG. 29 is a photo showing the trapping lines for oil droplets in the ultrasonic waves generated by an array of transducers.

Figure 30:
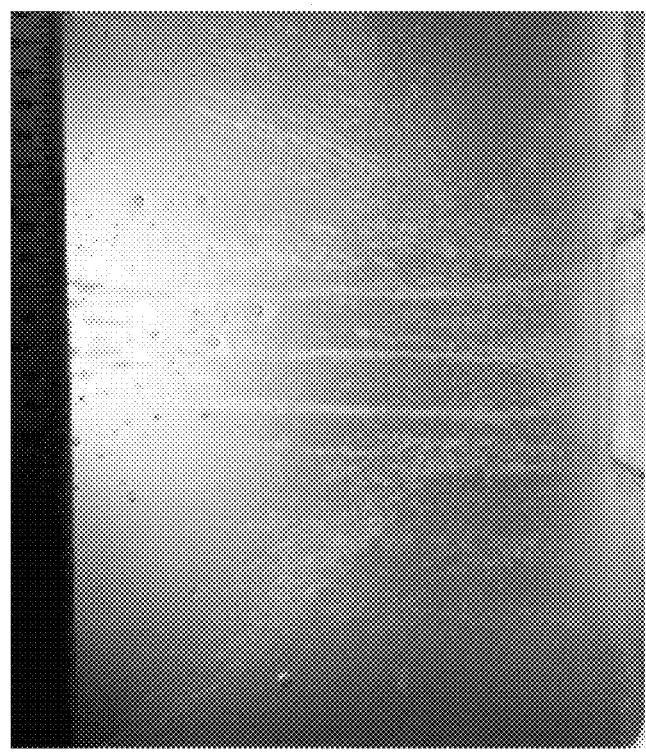

FIG. 30 is a photo showing the trapping lines for oil droplets in the ultrasonic waves generated by an array of transducers.

Figure 31:
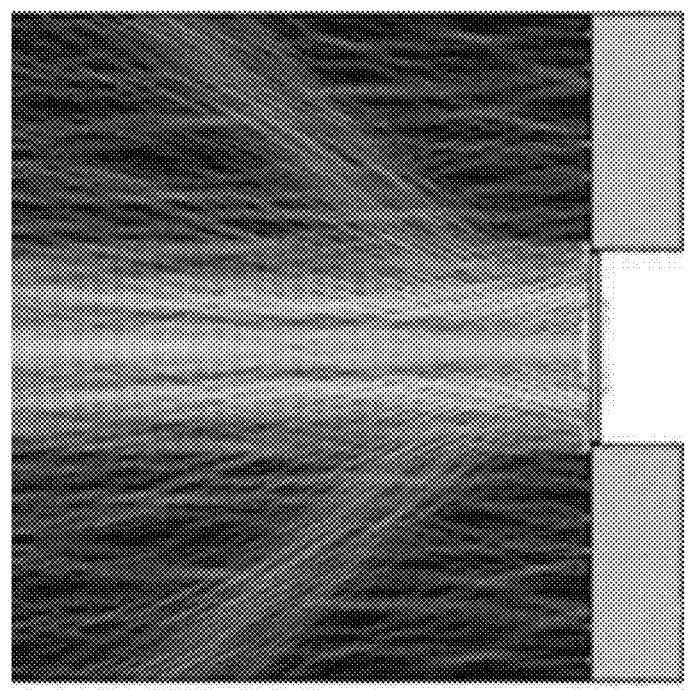

FIG. 31 is a computer simulation of acoustic pressure amplitude.

Figure 32:
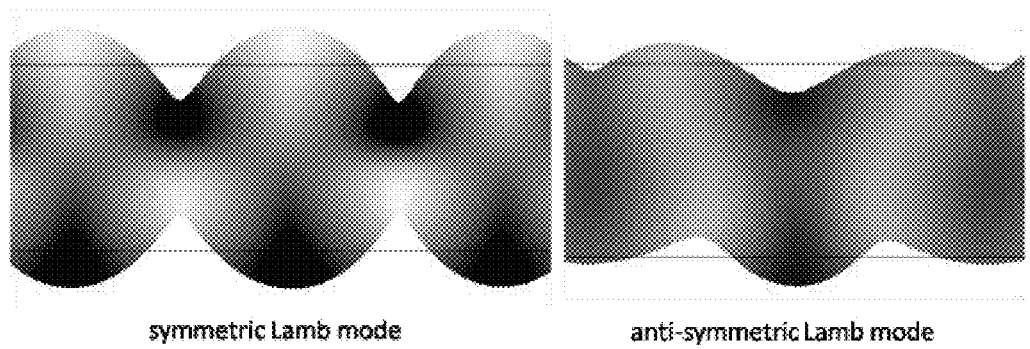

FIG. 32 shows a depiction of symmetric Lamb waves and anti-symmetric Lamb waves.

Figure 33:
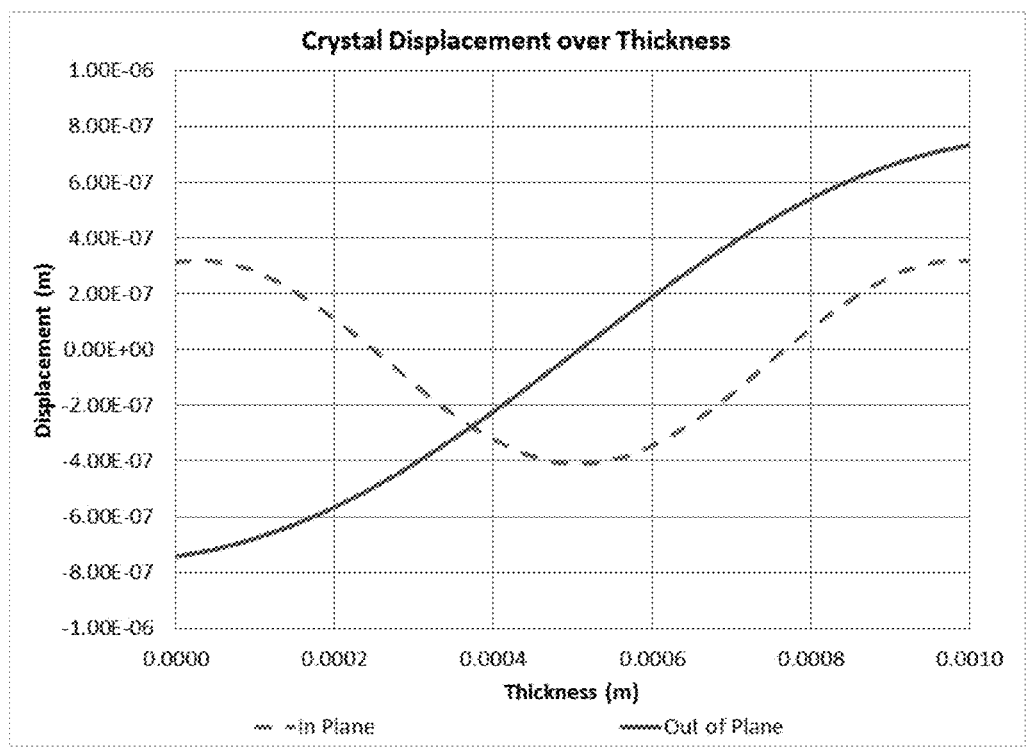

FIG. 33 shows the In-Plane and Out-of-Plane displacement of a crystal where composite waves are present.

Figure 34A:
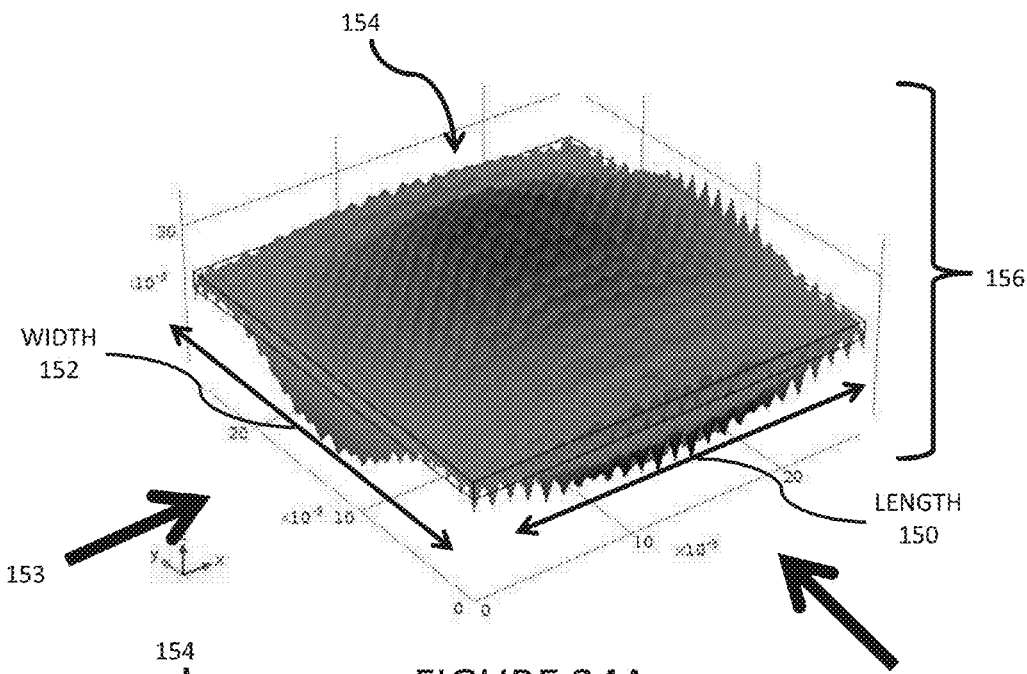
Figure 34B:
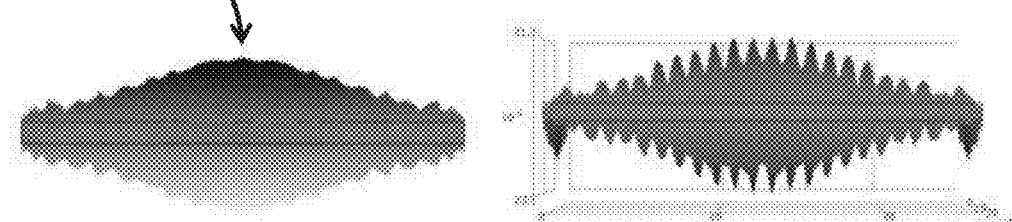
Figure 34C:
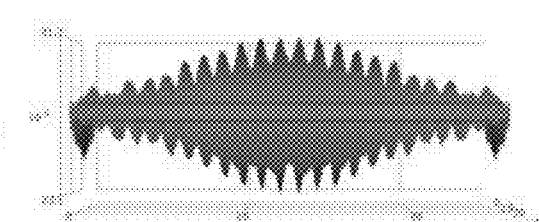
Figure 34D:
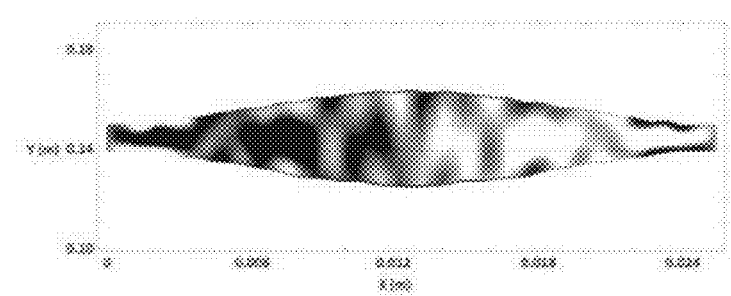

FIGS. 34A-34D illustrate the (1,1) vibration mode of a rectangular plate. FIG. 34A is a perspective view. FIG. 34B is the view along the length of the plate. FIG. 34C is the view along the width of the plate. FIG. 34D shows the in-plane displacement of the rectangular plate vibrating at the (1,1) mode.

Figure 35A:
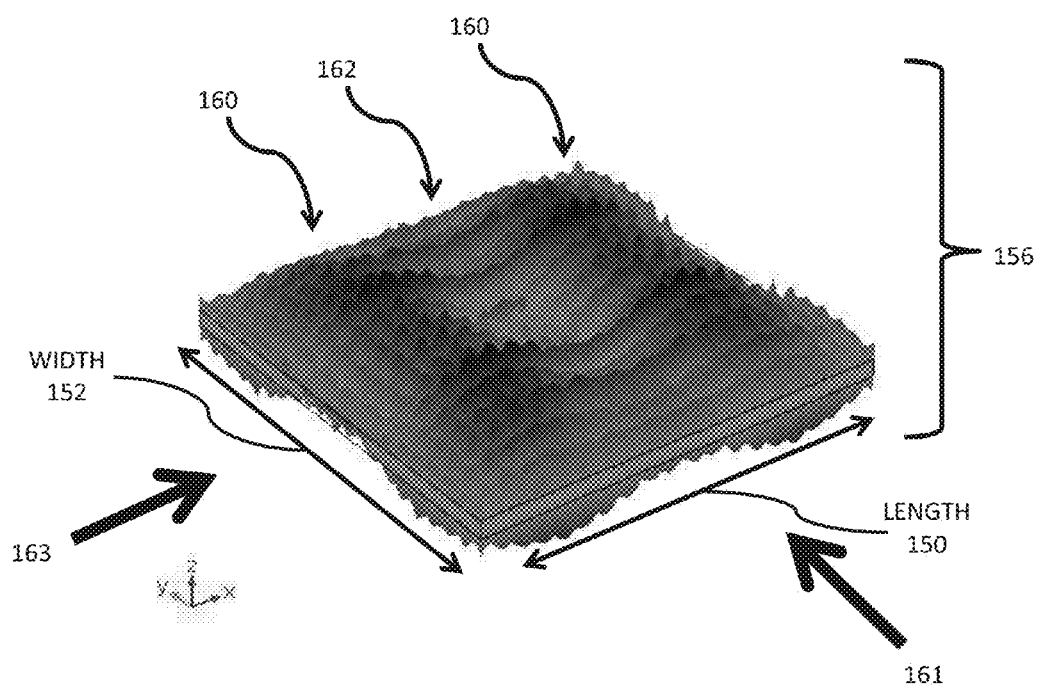
Figures 35B, 35C:
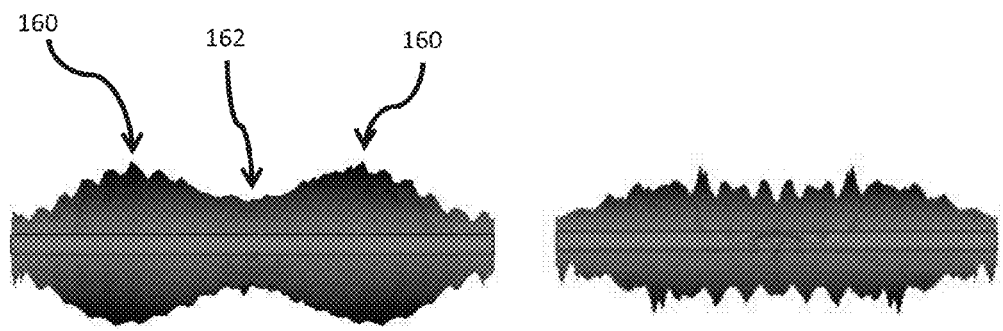

FIGS. 35A-35C illustrate the (1,2) vibration mode of a rectangular plate. FIG. 35A is a perspective view. FIG. 35B is the view along the length of the plate. FIG. 35C is the view along the width of the plate.

FIGS. 36A-36C illustrate the (2,1) vibration mode of a rectangular plate. FIG. 36A is a perspective view. FIG. 36B is the view along the length of the plate. FIG. 36C is the view along the width of the plate.

Figure 37A:
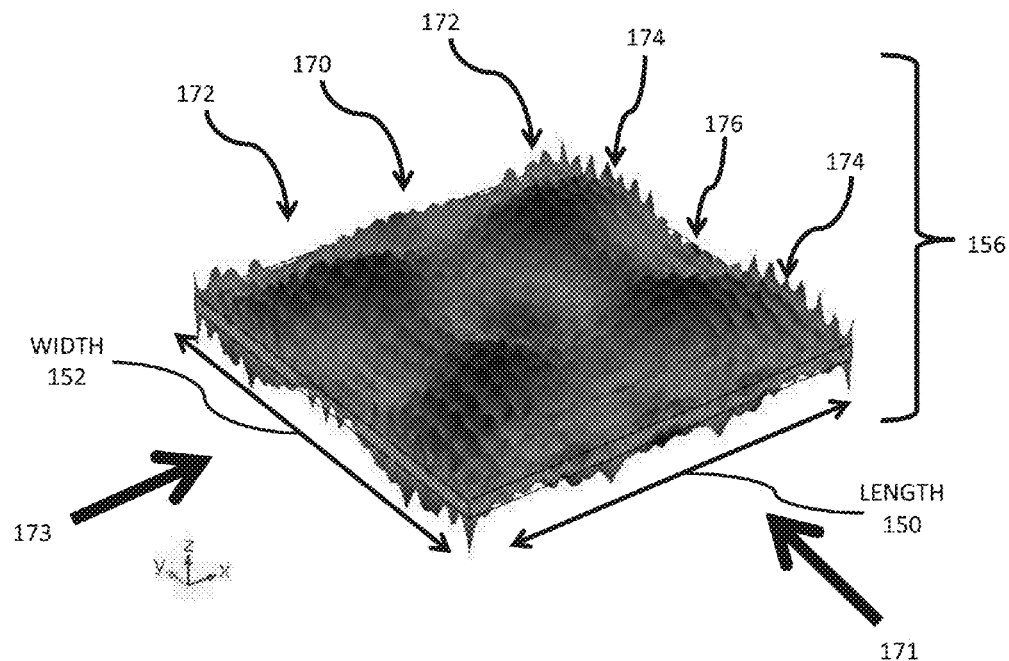
Figures 37B, 37C:
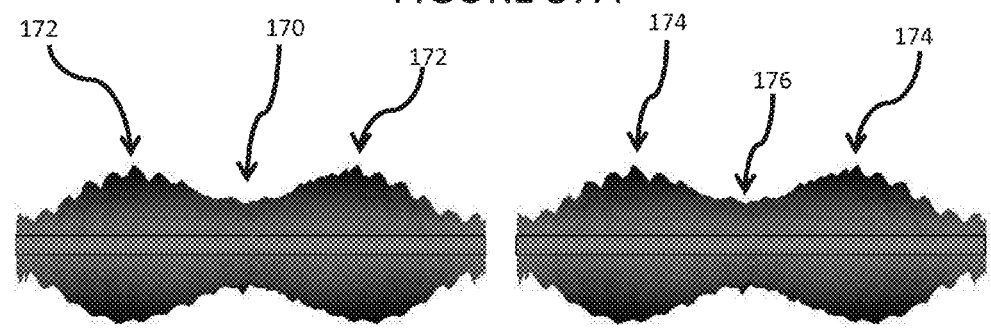

FIGS. 37A-37C illustrate the (2,2) vibration mode of a rectangular plate. FIG. 37A is a perspective view. FIG. 37B is the view along the length of the plate. FIG. 37C is the view along the width of the plate.

Figure 38A:
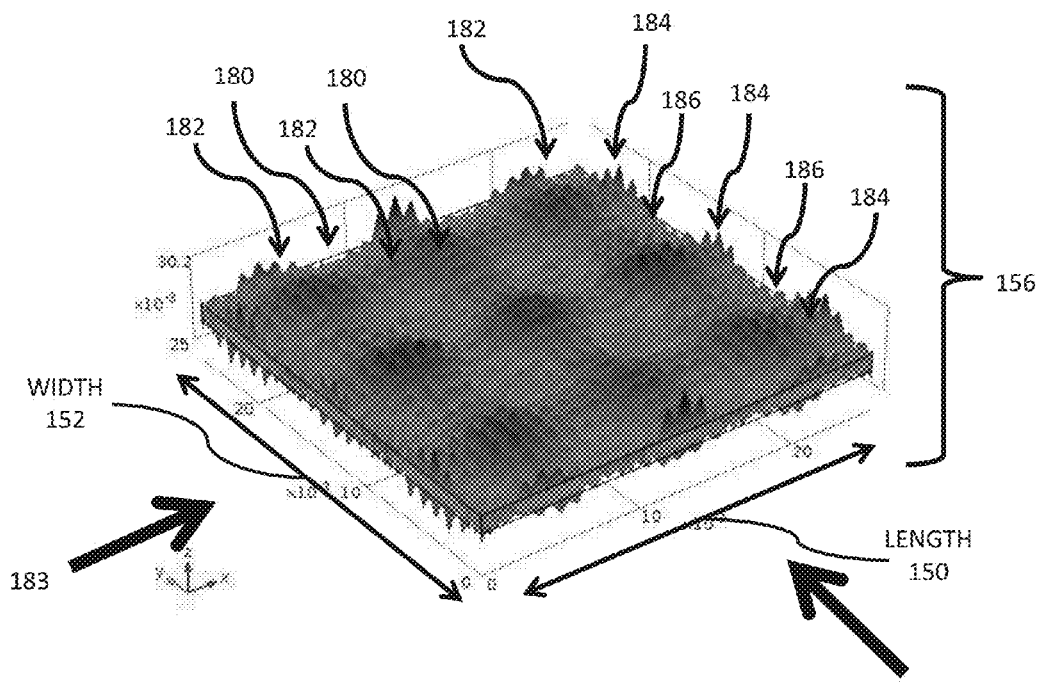
Figure 38B:
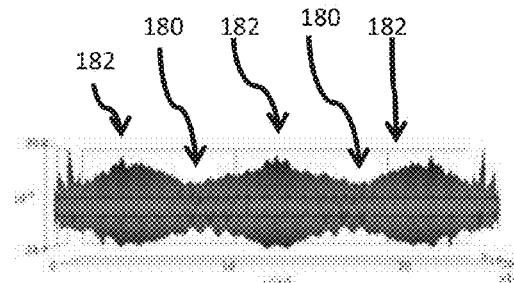
Figure 38C:
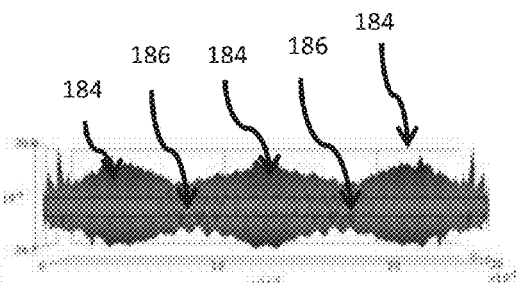
Figure 38D:
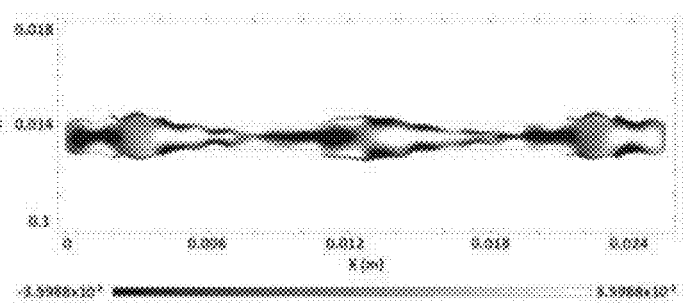

FIGS. 38A-38D illustrate the (3,3) vibration mode of a rectangular plate. FIG. 38A is a perspective view. FIG. 38B is the view along the width of the plate. FIG. 38C is the view along the length of the plate. FIG. 38D shows the in-plane displacement of the rectangular plate vibrating at the (3,3) mode.

FIG. 39A shows the pressure field created in water at a (1,1) vibration mode. FIG. 39B shows the pressure field created in water at a (2,2) vibration mode. FIG. 39C shows the pressure field created in water at a (3,3) vibration mode.

Figure 40A:
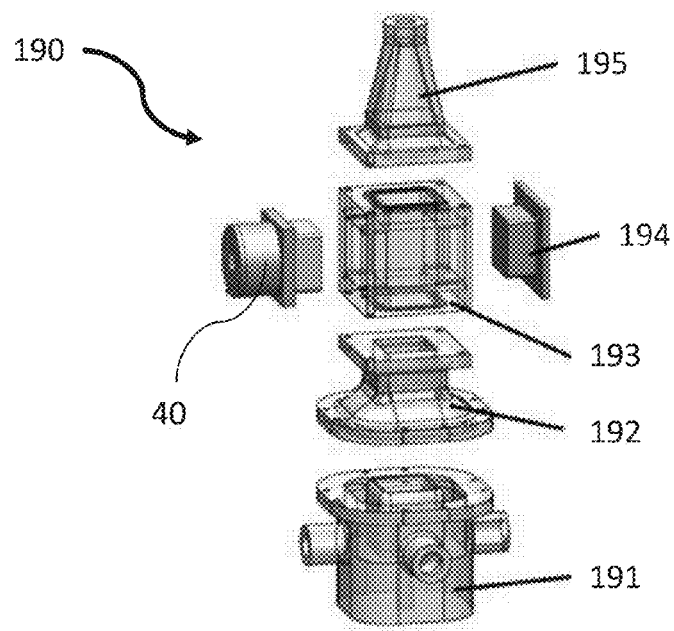

FIG. 40A shows an exploded view of an acoustophoretic separator used in Bio-Pharma applications.

Figure 40B:
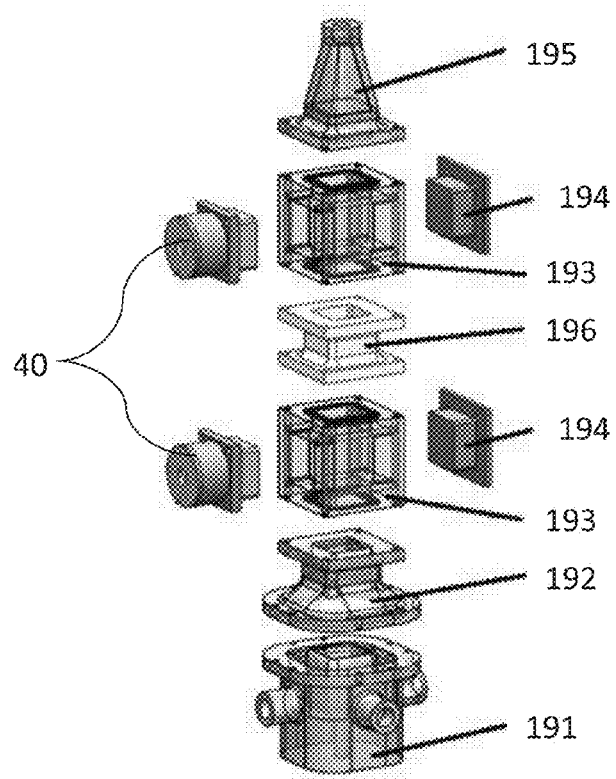

FIG. 40B shows an exploded view of a stacked acoustophoretic separator with two acoustic chambers.

Figure 41A:
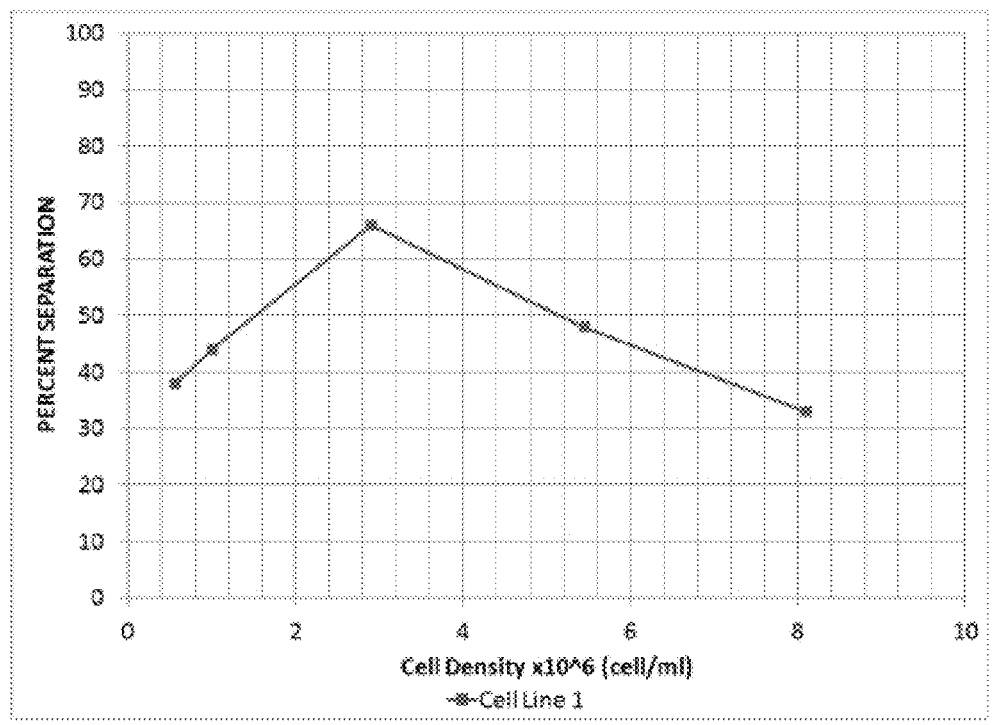

FIG. 41A is a graph showing the efficiency of removing cells from a medium using a Beckman Coulter Cell Viability Analyzer for one experiment.

Figure 41B:
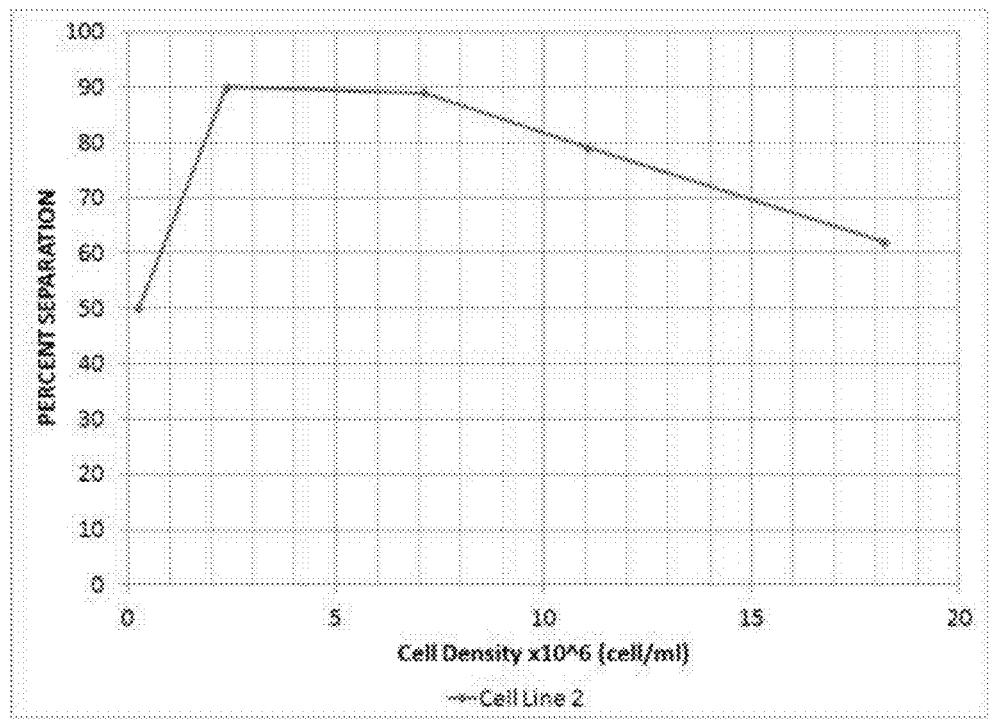

FIG. 41B is a graph showing the efficiency of removing cells from a medium using a Beckman Coulter Cell Viability Analyzer for another experiment.

DETAILED DESCRIPTION

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of."

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "above" and "below", or "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value less than 10.

Efficient separation technologies for multi-component liquid streams that eliminate any waste and reduce the required energy, and therefore promote a sustainable environment, are needed. Large volume flow rate acoustophoretic phase separator technology using ultrasonic standing waves provides the benefit of having no consumables, no generated waste, and a low cost of energy. The technology is efficient at removal of particles of greatly varying sizes, including separation of micron and sub-micron sized particles. Examples of acoustic filters/collectors utilizing acoustophoresis can be found in commonly owned U.S. patent application Ser. Nos. 12/947,757; 13/085,299; 13/216,049; and 13/216,035, the entire contents of each being hereby fully incorporated by reference.

The platform technology described herein provides an innovative solution that includes a large volume flow rate acoustophoretic phase separator based on ultrasonic standing waves with the benefit of having no consumables, no generated waste, and a low cost of energy. Acoustophoresis is a low-power, no-pressure-drop, no-clog, solid-state approach to particle removal from fluid dispersions: i.e., it is used to achieve separations that are more typically performed with porous filters, but it has none of the disadvantages of filters. In particular, the present disclosure provides systems that operate at the macro-scale for separations in flowing systems with high flow rates. The acoustic resonator is designed to create a high intensity three dimensional ultrasonic standing wave that results in an acoustic radiation force that is larger than the combined effects of fluid drag and buoyancy or gravity, and is therefore able to trap (i.e., hold stationary) the suspended phase to allow more time for the acoustic wave to increase particle concentration, agglomeration and/or coalescence. The present systems have the ability to create ultrasonic standing wave fields that can trap particles in flow fields with a linear velocity ranging from 0.1 mm/sec to velocities exceeding 1 cm/s. This technology offers a green and sustainable alternative for separation of secondary phases with a significant reduction in cost of energy. Excellent particle separation efficiencies have been demonstrated for particle sizes as small as one micron.

The acoustophoretic separation technology employs ultrasonic standing waves to trap, i.e., hold stationary, secondary phase particles in a host fluid stream. This is an important distinction from previous approaches where particle trajectories were merely altered by the effect of the acoustic radiation force. The scattering of the acoustic field off the particles results in a three dimensional acoustic radiation force, which acts as a three-dimensional trapping field. The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy/gravitational force, the particle is trapped within the acoustic standing wave field. The action of the acoustic forces on the trapped particles results in concentration, agglomeration and/or coalescence of particles and droplets. Additionally, secondary inter-particle forces, such as Bjerkness forces, aid in particle agglomeration. Heavier-than-the-host-fluid (i.e. denser than the host fluid) particles and/or fluids are separated through enhanced gravitational settling, and lighter-than-the-host-fluid particles and/or fluids are separated through enhanced buoyancy.

It is also possible to drive multiple ultrasonic transducers with arbitrary phasing. In other words, the multiple transducers may work to separate materials in a fluid stream while being out of phase with each other. Alternatively, a single ultrasonic transducer that has been divided into an ordered array may also be operated such that some components of the array will be out of phase with other components of the array.

Efficient and economic particle separation processes can be useful in many areas of energy generation, e.g., producing water, hydro-fracking, and bio-fuels, e.g, harvesting and dewatering. Acoustophoretic technology can be used to target accelerated capture of bacterial spores in water, oil-recovery, and dewatering of bio-oil derived from micro-algae. Current technology used in the oil recovery field does not perform well in recovery of small, i.e., less than 20 micron, oil droplets. However, the acoustophoretic systems described herein can enhance the capture and coalescence of small oil droplets, thereby shifting the particle size distribution resulting in an overall increased oil capture. To be useful, it is generally necessary to demonstrate large flow rates at a level of 15-20 gallons per minute (GPM) per square foot (cross-sectional area). Another goal is the increased capture of oil droplets with a diameter of less than 20 microns.

Acoustophoretic separation can also be used to aid such applications as advanced bio-refining technology to convert low-cost readily available non-food biomass (e.g. municipal solid waste and sewage sludge) into a wide array of chemicals and secondary alcohols that can then be further refined into renewable gasoline, jet fuel, or diesel. A water treatment technology is used to de-water the fermentation broth and isolate valuable organic salts for further processing into fuels. The dewatering process is currently done through an expensive and inefficient ultra-filtration method that suffers from frequent fouling of the membranes, a relatively low concentration factor, and a high capital and operating expense. Acoustophoretic separation can filter out particles with an incoming particle size distribution that spans more than three orders of magnitude, namely from 600 microns to 0.3 microns, allowing improvements in the concentration of the separated broth with a lower capital and operational expense. Some other applications are in the areas of wastewater treatment, grey water recycling, and water production.

Acoustophoretic separation is also useful for the harvesting, oil-recovery, and dewatering of micro-algae for conversion into bio-oil. Current harvesting, oil recovery, and dewatering technologies for micro-algae suffer from high operational and capital expenses. Current best estimates put the price of a barrel of bio-oil derived from micro-algae at a minimum of $200.00 per barrel. There is a need in the art of micro-algae biofuel for technologies that improve harvesting, oil-recovery, and dewatering steps of this process. Acoustophoretic separation technology meets this need.

Other applications are in the area of life sciences and medical applications, such as the separation of lipids from red blood cells. This can be of critical importance during cardiopulmonary bypass surgery, which involves suctioning shed mediastinal blood. Lipids are unintentionally introduced to the bloodstream when blood is re-transfused to the body. Lipid micro-emboli can travel to the brain and cause various neuro-cognitive disorders. Therefore, there is a need to cleanse the blood. Existing methods are currently inefficient or harmful to red blood cells.

One specific application for the acoustophoresis device is in the processing of bioreactor materials. In a fed batch bioreactor, it is important at the end of the production cycle to filter all of the cells and cell debris from the expressed materials that are in the fluid stream. The expressed materials are composed of biomolecules such as recombinant proteins or monoclonal antibodies, and are the desired product to be recovered. Through the use of acoustophoresis, the separation of the cells and cell debris is very efficient and leads to very little loss of the expressed materials. This is an improvement over the current filtration processes (depth filtration, tangential flow filtration, centrifugation), which show limited efficiencies at high cell densities, so that the loss of the expressed materials in the filter beds themselves can be up to 5% of the materials produced by the bioreactor. The use of mammalian cell culture include Chinese hamster ovary (CHO), NS0 hybridoma cells, baby hamster kidney (BHK) cells, and human cells has proven to be a very efficacious way of producing/expressing the recombinant proteins and monoclonal antibodies required of today's pharmaceuticals. The filtration of the mammalian cells and the mammalian cell debris through acoustophoresis aids in greatly increasing the yield of the fed batch bioreactor.

Another type of bioreactor, a perfusion reactor, uses continuous expression of the target protein or monoclonal antibodies from the CHO cells. This enables a much smaller footprint in faster production cycle. The use of acoustophoresis to hold the CHO cells in a fluid stream as they are producing/expressing the proteins is a very efficient and closed loop way of production. It also allows for a maximum production efficiency of the proteins and monoclonal antibodies in that none of the materials are lost in a filter bed.

In the fed batch bioreactor process, the acoustophoresis device uses singular or multiple standing waves to trap the cells and cell debris. The cells and cell debris, having a positive contrast factor, move to the nodes (as opposed to the anti-nodes) of the standing wave. As the cells and cell debris agglomerate at the nodes of the standing wave, there is also a physical scrubbing of the fluid stream that occurs whereby more cells are trapped as they come in contact with the cells that are already held within the standing wave. When the cells in the standing wave agglomerate to the extent where the mass is no longer able to be held by the acoustic wave, the aggregated cells and cell debris that have been trapped fall out of the fluid stream through gravity, and can be collected separately. To aid this gravitational settling of the cells and cell debris, the standing wave may be interrupted to allow all of the cells to fall out of the fluid stream that is being filtered from the fed batch bioreactor.

Figure 3:
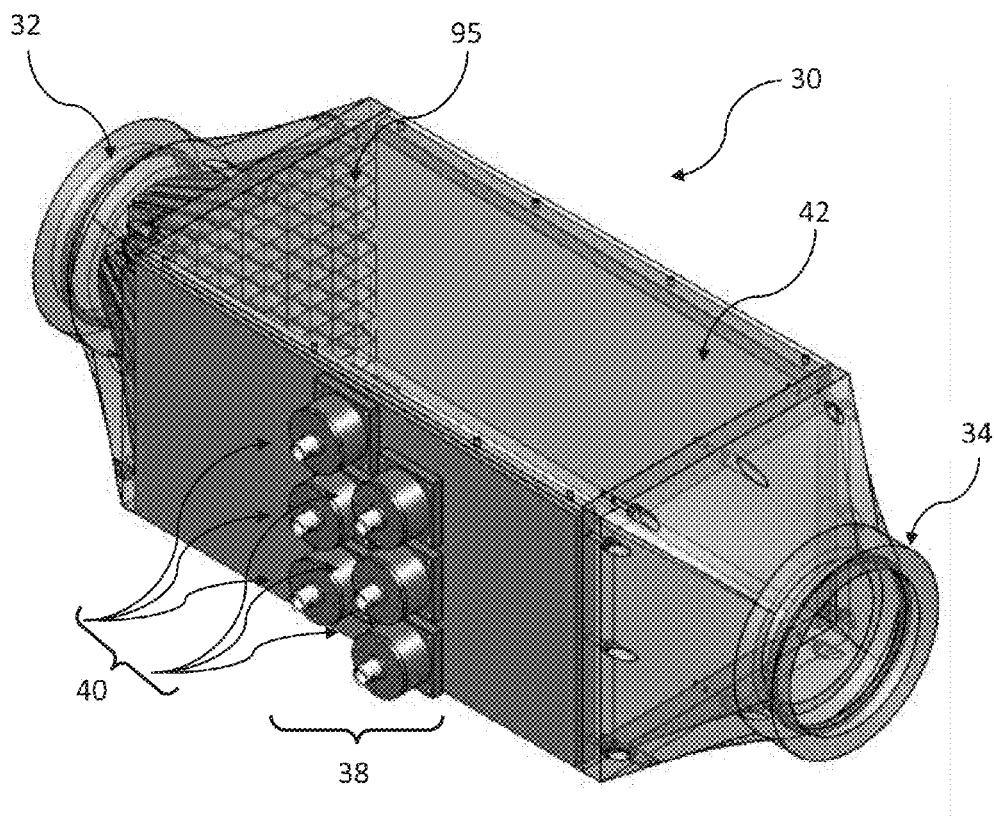
FIG. 3 shows an acoustophoretic separator having a plurality of transducers.

Particular embodiments also focus on the capture and growth of sub-20-micron oil droplets. At least 80% of the volume of sub-20-micron droplets are captured and then grown to droplets that are bigger than 20 microns. The process involves the trapping of the oil droplets in the acoustic standing wave, coalescence of many small trapped droplets, and eventually release of the larger droplets when the acoustic trapping force becomes smaller than the buoyancy force. This design is shown in FIG. 3 where separation of contaminants is not required.

Advanced multi-physics and multiple length scale computer models and high frequency (MHz), high-power, and high-efficiency ultrasonic drivers with embedded controls have been combined to arrive at new designs of acoustic resonators driven by arrays of piezoelectric transducers, resulting in acoustophoretic separation devices that far surpass current capabilities.

Desirably, such transducers generate a three-dimensional standing wave in the fluid that exerts a lateral force on the suspended particles/secondary fluid to accompany the axial force so as to increase the particle trapping capabilities of a acoustophoretic system. Typical results published in literature state that the lateral force is two orders of magnitude smaller than the axial force. In contrast, the technology disclosed in this application provides for a lateral force to be of the same order of magnitude as the axial force.

As defined herein, impurities include particles or fluids distinct from the host fluid. The acoustic resonator 10 is designed to maintain a high intensity three-dimensional acoustic standing wave. The system is driven by a function generator and amplifier (not shown). The system performance is monitored and controlled by a computer.

It may be necessary, at times, due to acoustic streaming, to modulate the frequency or voltage amplitude of the standing wave. This may be done by amplitude modulation and/or by frequency modulation. The duty cycle of the propagation of the standing wave may also be utilized to achieve certain results for trapping of materials. In other words, the acoustic beam may be turned on and shut off at different frequencies to achieve desired results.

Figure 1A:
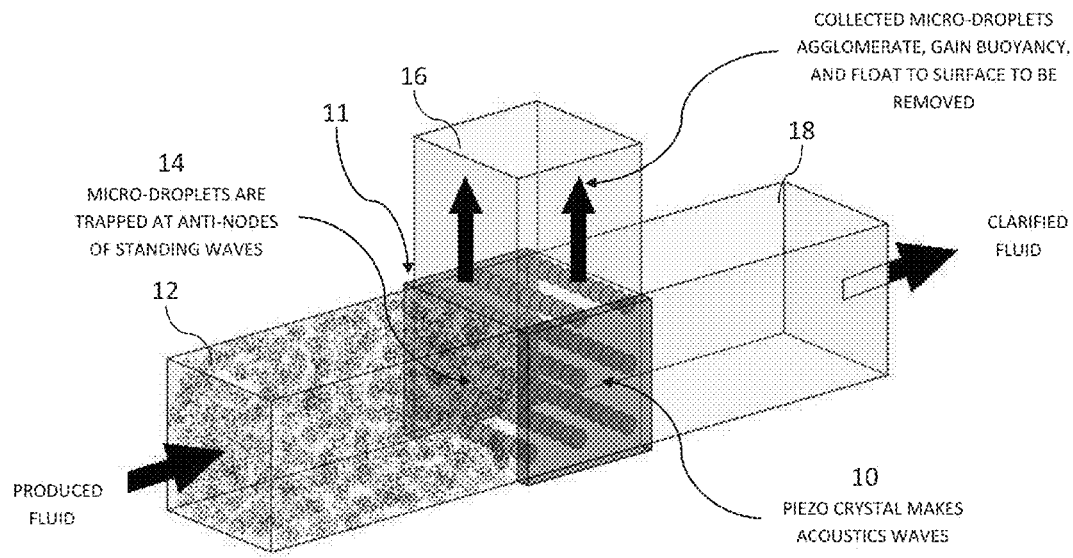
FIG. 1A is a diagram illustrating the function of an acoustophoretic separator with a second fluid or particle less dense than the host fluid.

A diagrammatic representation of an embodiment for removing oil or other lighter-than-water material is shown in FIG. 1A. Excitation frequencies typically in the range from hundreds of kHz to 10s of MHz are applied by transducer 10. One or more standing waves are created between the transducer 10 and the reflector 11. Microdroplets 12 are trapped in standing waves at the pressure anti-nodes 14 where they agglomerate, aggregate, clump, or coalesce, and, in the case of buoyant material, float to the surface and are discharged via an effluent outlet 16 located above the flow path. Clarified water is discharged at outlet 18. The acoustophoretic separation technology can accomplish multi-component particle separation without any fouling at a much reduced cost.

Figure 1B:
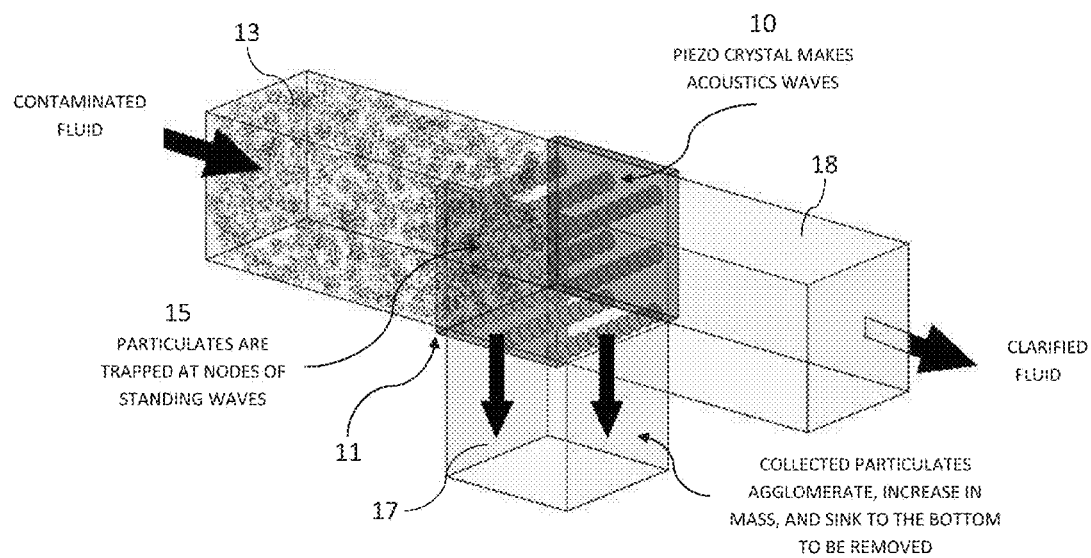
FIG. 1B is a diagram illustrating the function of an acoustophoretic separator with a second fluid or particle denser than the host fluid.

A diagrammatic representation of an embodiment for removing contaminants or other heavier-than-water material is shown in FIG. 1B. Excitation frequencies typically in the range from hundreds of kHz to 10s of MHz are applied by transducer 10. Contaminants in the incoming water 13 are trapped in standing waves at the pressure nodes 15 where they agglomerate, aggregate, clump, or coalesce, and, in the case of heavier material, sink to the bottom collector and are discharged via an effluent outlet 17 located below the flow path. Clarified water is discharged at outlet 18.

Figure 2A:
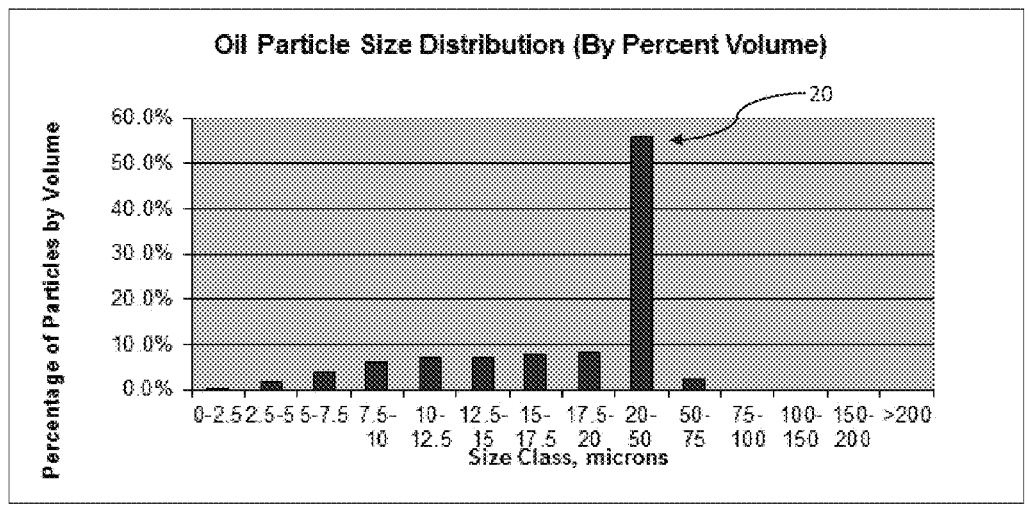
FIG. 2A shows a cell size distribution produced by a Jorin ViPA Particle Size Analyzer when there was no acoustic field present. The horizontal axis is the size class, in microns, and the vertical axis is the percent of particles sampled by volume.

FIG. 2A shows a particle size distribution that was measured as an oil-water emulsion passed through an acoustophoretic system without an acoustic field activated. The peak particle size 20 is between 20-50 microns in size without the acoustic field being activated. These droplets are typically very difficult to separate by conventional means, such as, e.g., hydrocyclones.

Figure 2B:
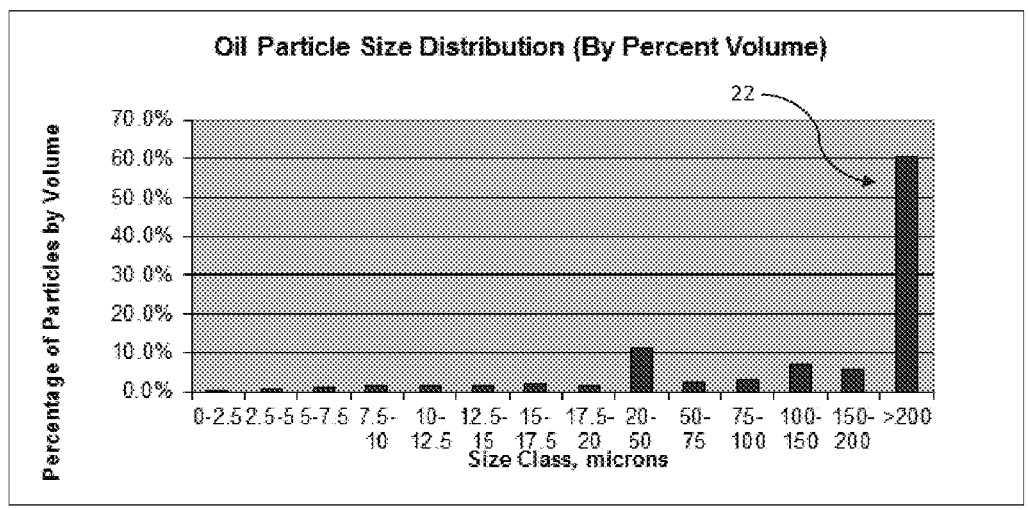
FIG. 2B shows a cell size distribution produced by a Jorin ViPA Particle Size Analyzer when there was an acoustic field present. The horizontal axis is the size class, in microns, and the vertical axis is the percent of particles sampled by volume.

FIG. 2B shows a similar particle size distribution that was measured after an oil-water emulsion passed through an acoustophoretic system with the acoustic field activated. The peak particle size 22 is greater than 200 microns in size with the acoustic field being activated. The results clearly show a significant amount of oil droplet growth, i.e., many sub-20 micron droplets coalesced, agglomerated, or clumped into larger droplets (bigger than 20 micron) as a result of the action of the acoustic forces on the droplets.

FIG. 3 shows another embodiment of an acoustophoretic particle separator 30. The acoustophoretic separator 30 has an inlet 32 and an outlet 34. The inlet 32 is fitted with a nozzle or diffuser 90 having a honeycomb 95 to facilitate the development of plug flow. The acoustophoretic separator 30 has an array 38 of transducers 40, in this case six transducers all arranged on the same wall. The transducers are arranged so that they cover the entire cross-section of the flow path. The acoustophoretic separation system of FIG. 3 has, in certain embodiments, a square cross section of 6 inches×6 inches which operates at flow rates of up to 3 gallons per minute (GPM), or a linear velocity of 8 mm/sec. The transducers 40 are six PZT-8 (Lead Zirconate Titanate) transducers with a 1 inch diameter and a nominal 2 MHz resonance frequency. Each transducer consumes about 28 W of power for droplet trapping at a flow rate of 3 GPM. This translates in an energy cost of 0.25 kW hr/m$^3$. This is an indication of the very low cost of energy of this technology. Desirably, each transducer is powered and controlled by its own amplifier. The application for this embodiment is to shift the particle size distribution through agglomeration, aggregation, clumping or coalescing of the micron-sized oil droplets into much larger droplets, as evident in FIG. 2A and FIG. 2B.

Figures 4A, 4B:
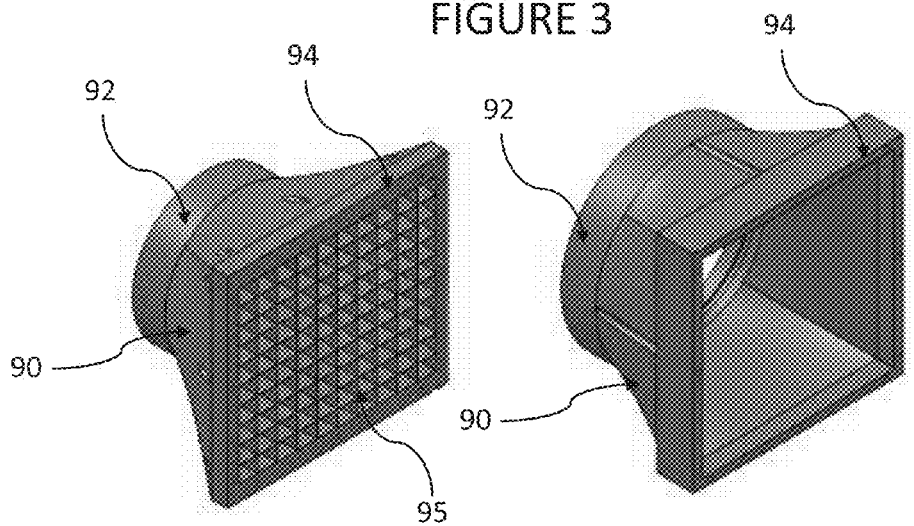
FIG. 4A is a detail view of a diffuser used as an inlet in the separator of FIG. 3.
FIG. 4B is a detail view of an alternate inlet diffuser that can be used with the separator of FIG. 3.

FIG. 4A and FIG. 4B show two different diffusers that can be used at the inlet of the acoustophoretic separator. The diffuser 90 has an entrance 92 (here with a circular shape) and an exit 94 (here with a square shape). The diffuser of FIG. 4A is illustrated in FIG. 3. FIG. 4A includes a grid or honeycomb 95, whereas FIG. 4B does not. The grid helps ensure uniform flow.

Figure 5:
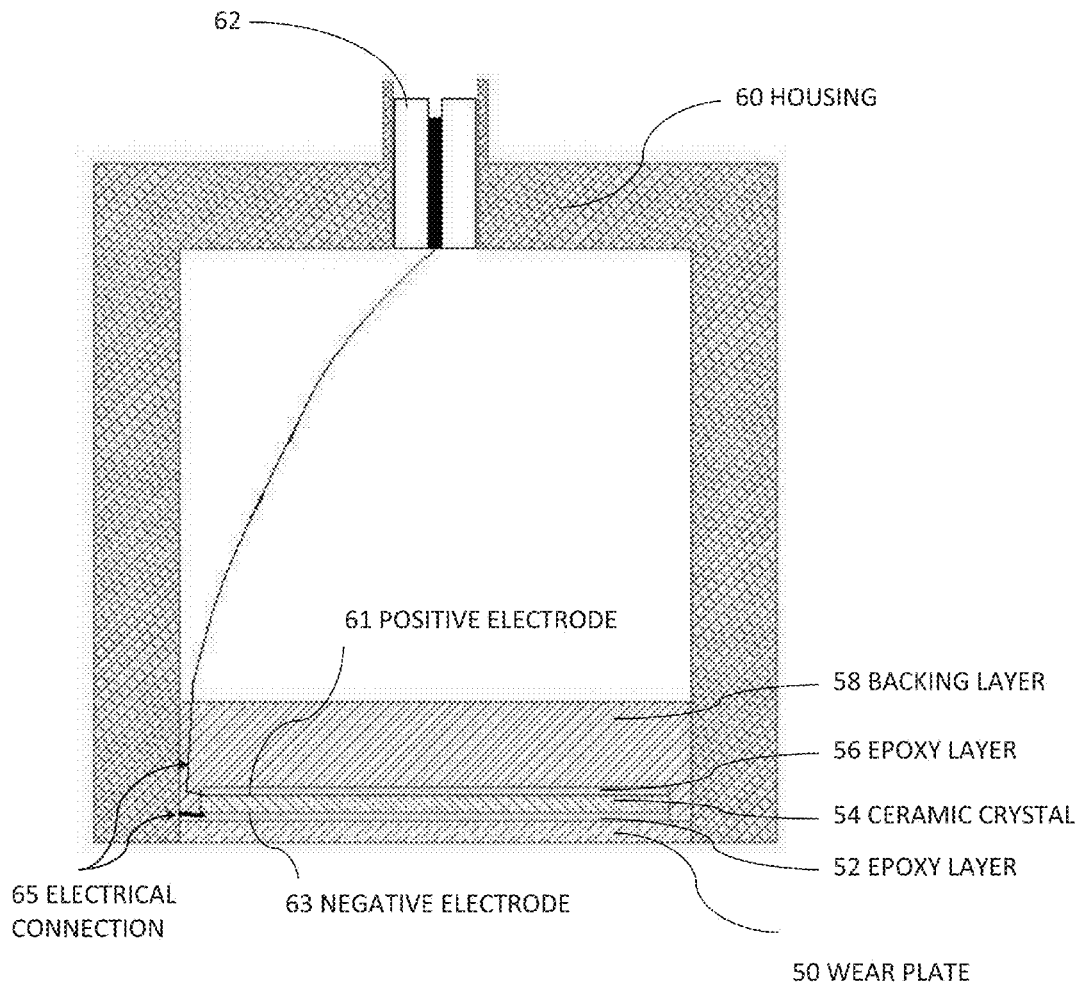
FIG. 5 is a cross-sectional diagram of a conventional ultrasonic transducer.

FIG. 5 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

Figure 6:
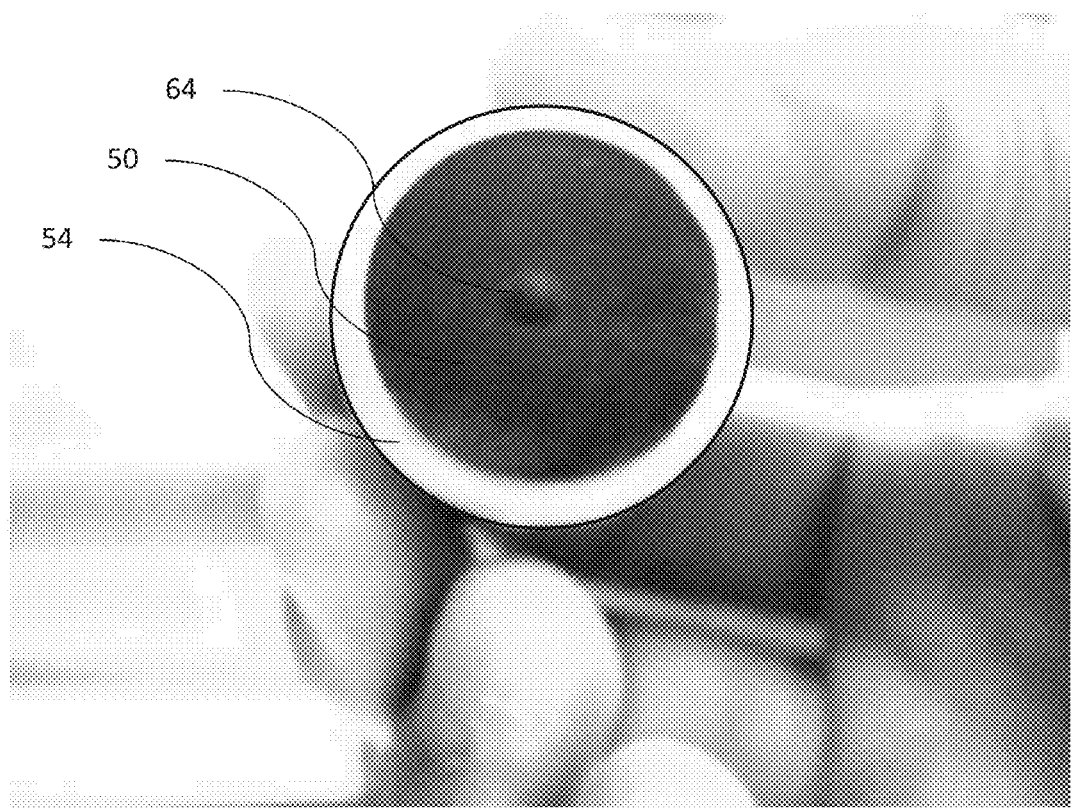
FIG. 6 is a picture of a wear plate of a conventional transducer.

FIG. 6 is a photo of a wear plate 50 with a bubble 64 where the wear plate has pulled away from the ceramic crystal surface due to the oscillating pressure and heating.

Figure 7A:
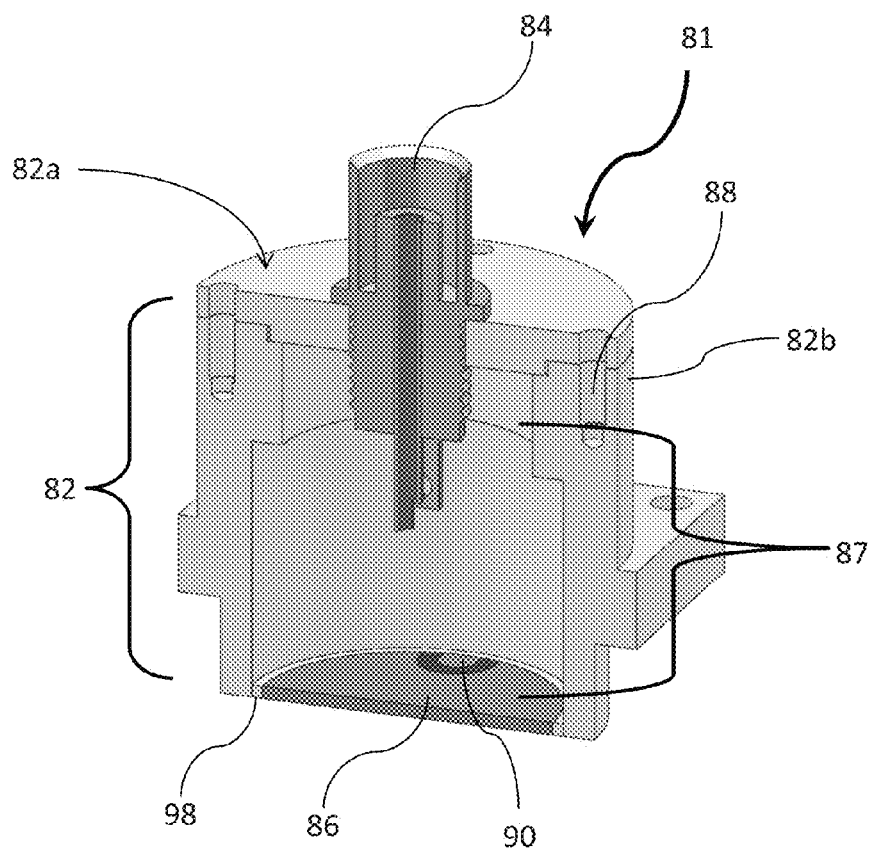
FIG. 7A is a cross-sectional diagram of an ultrasonic transducer of the present disclosure. An air gap is present within the transducer, and no backing layer or wear plate is present.

FIG. 7A is a cross-sectional view of an ultrasonic transducer 81 of the present disclosure, which can be used with the acoustophoretic separator of FIG. 3. Transducer 81 has an aluminum housing 82. A PZT crystal 86 defines the bottom end of the transducer, and is exposed from the exterior of the housing. The crystal is supported on its perimeter by a small elastic layer 98, e.g. silicone or similar material, located between the crystal and the housing. Put another way, no wear layer is present.

Figure 7B:
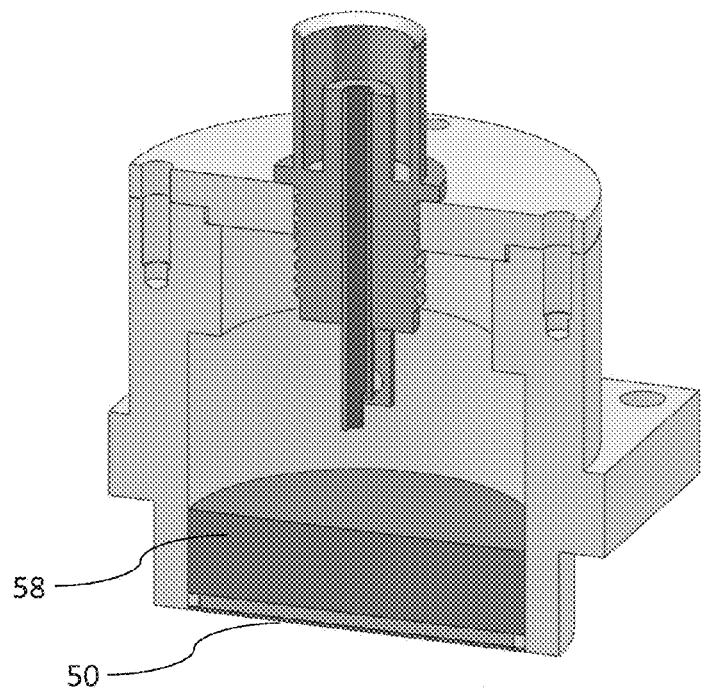
FIG. 7B is a cross-sectional diagram of an ultrasonic transducer of the present disclosure. An air gap is present within the transducer, and a backing layer and wear plate are present.

Screws (not shown) attach an aluminum top plate 82a of the housing to the body 82b of the housing via threads 88. The top plate includes a connector 84 to pass power to the PZT crystal 86. The bottom and top surfaces of the PZT crystal 86 are each connected to an electrode (positive and negative), such as silver or nickel. A wrap-around electrode tab 90 connects to the bottom electrode and is isolated from the top electrode. Electrical power is provided to the PZT crystal 86 through the electrodes on the crystal, with the wrap-around tab 90 being the ground connection point. Note that the crystal 86 has no backing layer or epoxy layer as is present in FIG. 5. Put another way, there is an air gap 87 in the transducer between aluminum top plate 82a and the crystal 86 (i.e. the air gap is completely empty). A minimal backing 58 and/or wear plate 50 may be provided in some embodiments, as seen in FIG. 7B.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes with a high Q-factor. The vibrating ceramic crystal/disk is directly exposed to the fluid flowing through the flow chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines. See the discussion below with respect to FIGS. 20-21D.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylylene) (e.g. Parylene) or other polymer. Organic and biocompatible coatings such as silicone or polyurethane are also usable as a wear surface.

In the present systems, the system is operated at a voltage such that the particles are trapped in the ultrasonic standing wave, i.e., remain in a stationary position. The particles are collected in along well defined trapping lines, separated by half a wavelength. Within each nodal plane, the particles are trapped in the minima of the acoustic radiation potential. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. In systems using typical transducers, the radial or lateral component of the acoustic radiation force is typically several orders of magnitude smaller than the axial component of the acoustic radiation force. On the contrary, the lateral force in the separators shown in FIG. 1A, FIG. 1B, FIG. 3 and FIG. 27 can be significant, on the same order of magnitude as the axial force component, and is sufficient to overcome the fluid drag force at linear velocities of up to 1 cm/s. As discussed above, the lateral force can be increased by driving the transducer in higher order mode shapes, as opposed to a form of vibration where the crystal effectively moves as a piston having a uniform displacement. The acoustic pressure is proportional to the driving voltage of the transducer. The electrical power is proportional to the square of the voltage.

In embodiments, the pulsed voltage signal driving the transducer can have a sinusoidal, square, sawtooth, or triangle waveform; and have a frequency of 500 kHz to 10 MHz. The pulsed voltage signal can be driven with pulse width modulation, which produces any desired waveform. The pulsed voltage signal can also have amplitude or frequency modulation start/stop capability to eliminate streaming.

Figure 8:
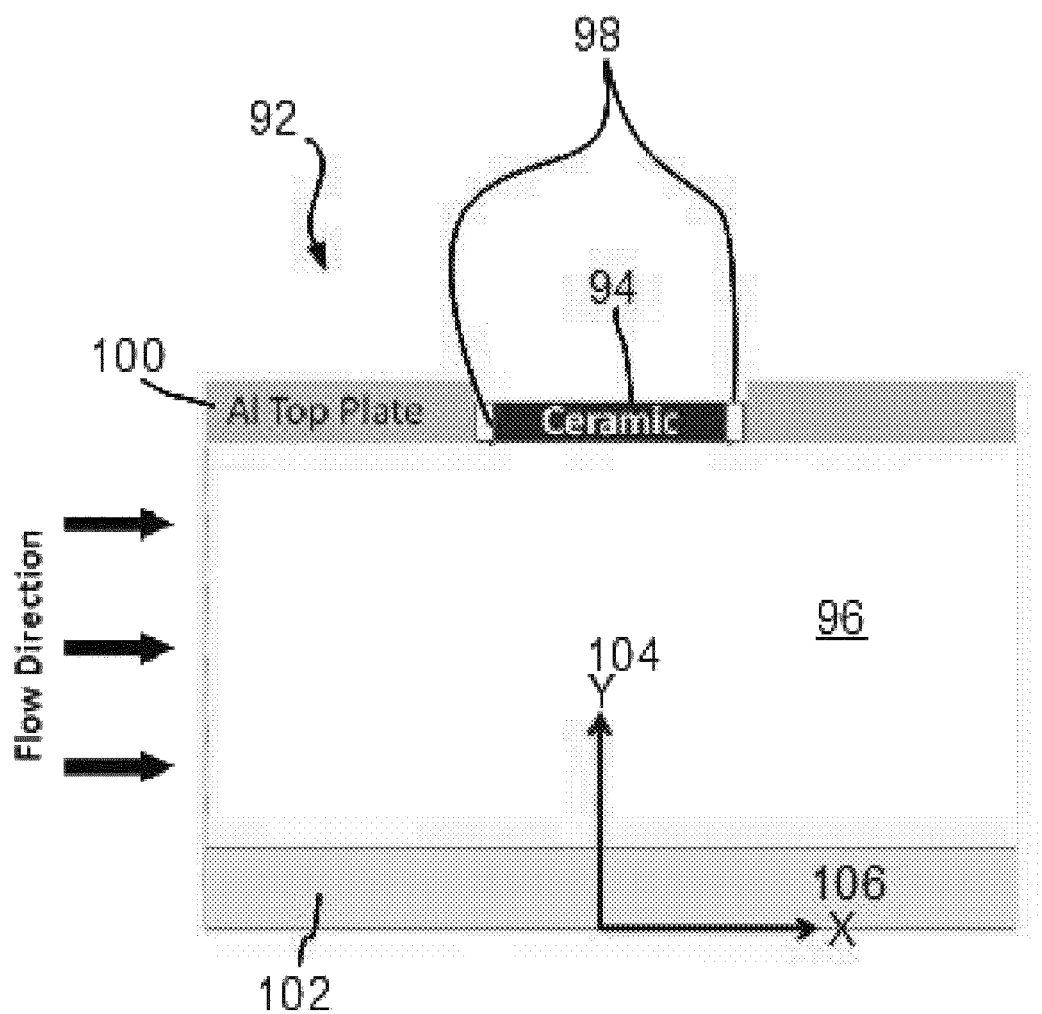
FIG. 8 is a computer model of an acoustophoretic separator simulated to generate FIG. 9 and FIGS. 11-17.

FIG. 8 is a computer model of an acoustophoretic separator 92 simulated to produce FIGS. 9A-9D and FIGS. 11-17. The piezo ceramic crystal 94 is in direct contact with the fluid in the water channel 96. A layer of silicon 98 is between the crystal 94 and the aluminum top plate 100. A reflector 102 reflects the waves to create standing waves. The reflector is made of a high acoustic impedance material such as steel or tungsten, providing good reflection. For reference, the Y-axis 104 will be referred to as the axial direction. The X-axis 106 will be referred to as the radial or lateral direction. The acoustic pressure and velocity models were calculated including piezo-electric models of the PZT transducer, linear elastic models of the surrounding structure (e.g. reflector plate and walls), and a linear acoustic model of the waves in the water column. The radiation force acting on a suspended particle was calculated using Gor'kov's formulation. The particle and fluid material properties, such as density, speed of sound, and particle size, are entered into the program, and used to determine the monopole and dipole scattering contributions. The acoustic radiation force is determined by performing a gradient operation on the field potential U, which is a function of the volume of the particle and the time averaged potential and kinetic energy of the acoustic field.

In a typical experiment, the system is operated at a voltage such that the particles are trapped in the ultrasonic standing wave, i.e., remain in a stationary position. The axial component of the acoustic radiation force drives the particles, with a positive contrast factor, to the pressure nodal planes, whereas particles with a negative contrast factor are driven to the pressure anti-nodal planes. The radial or lateral component of the acoustic radiation force is the force that traps the particle. It therefore must be larger than the combined effect of fluid drag force and gravitational force. For small particles or emulsions the drag force FD can be expressed as:

$$\vec{F}_D = 4\pi\mu_f R_p (\vec{U}_f - \vec{U}_p) \left[ \frac{1 + \frac{3}{2}\hat{\mu}}{1 + \hat{\mu}} \right],$$

where $U_f$ and $U_p$ are the fluid and particle velocity, $R_p$ is the particle radius, $\mu_f$ and $\mu_p$ are the dynamic viscosity of the fluid and particle, and $\hat{\mu}=\mu_p/\mu_f$ is the ratio of dynamic viscosities. The buoyancy force $F_B$ is expressed as:

$$F_B = \tfrac{4}{3}\pi R_p^3 (\rho_f - \rho_p).$$

For a particle to be trapped in the ultrasonic standing wave, the force balance on the particle must be zero, and therefore an expression for lateral acoustic radiation force $F_{LRF}$ can be found, which is given by:

$$F_{LRF} = F_D + F_B.$$

For a particle of known size and material property, and for a given flow rate, this equation can be used to estimate the magnitude of the lateral acoustic radiation force.

The theoretical model that is used to calculate the acoustic radiation force is the formulation developed by Gor'kov. The primary acoustic radiation force $F_A$ is defined as a function of a field potential U, $F_A = -\nabla(U)$,
where the field potential U is defined as $$U = V_0 \left[ \frac{\langle p^2 \rangle}{2\rho_f c_f^2} f_1 - \frac{3\rho_f \langle u^2 \rangle}{4} f_2 \right],$$

and $f_1$ and $f_2$ are the monopole and dipole contributions defined by $$f_1 = 1 - \frac{1}{\Lambda \sigma^2}, \quad f_2 = \frac{2(\Lambda - 1)}{2\Lambda + 1},$$

where p is the acoustic pressure, u is the fluid particle velocity, $\Lambda$ is the ratio of particle density $\rho_p$ to fluid density $\rho_f$, $\sigma$ is the ratio of particle sound speed $c_p$ to fluid sound speed $C_f$, and $V_o$ is the volume of the particle. For a one dimensional standing wave, where the acoustic pressure is expressed as $$p = A\cos(kx)\cos(\omega t),$$

where A is the acoustic pressure amplitude, k is the wavenumber, and w is the angular frequency. In this case, there is only the axial component of the acoustic radiation force $F_{ARF}$, which is found to be $$F_{ARF} = V_0 k X \frac{A^2}{4\rho_f c_f^2} \sin(2kx),$$

where X is the contrast factor given by $$X = \left( \frac{5\Lambda - 2}{1 + 2\Lambda} - \frac{1}{\sigma^2 \Lambda} \right).$$

Particles with a positive contrast factor will be driven to the pressure nodal planes, and particles with a negative contrast factor will be driven to the pressure anti-nodal planes.

Gor'kov's theory is limited to particle sizes that are small with respect to the wavelength of the sound fields in the fluid and the particle, and it also does not take into account the effect of viscosity of the fluid and the particle on the radiation force. Additional numerical models have been developed for the calculation of the acoustic radiation force for a particle without any restriction as to particle size relative to wavelength. These models also include the effect of fluid and particle viscosity, and therefore are a more accurate calculation of the acoustic radiation force. The models that were implemented are based on the theoretical work of Yurii Ilinskii and Evgenia Zabolotskaya.

Figure 9A:
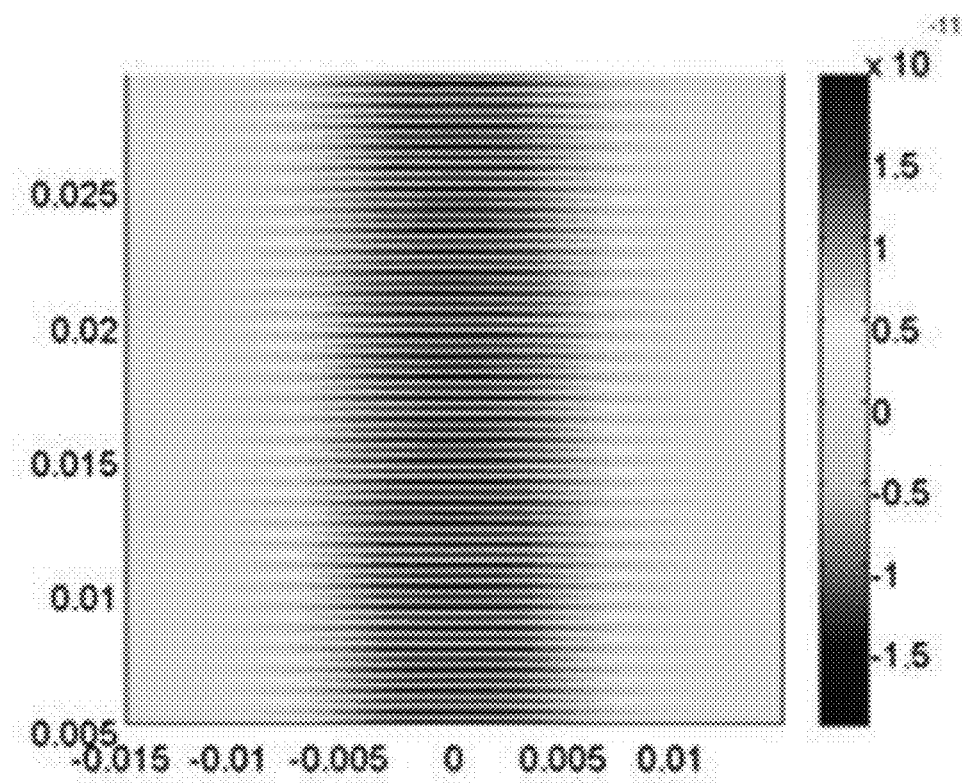
FIGS. 9A-9D show simulations of the forces on a particle in an acoustophoretic separator.
Figure 9B:
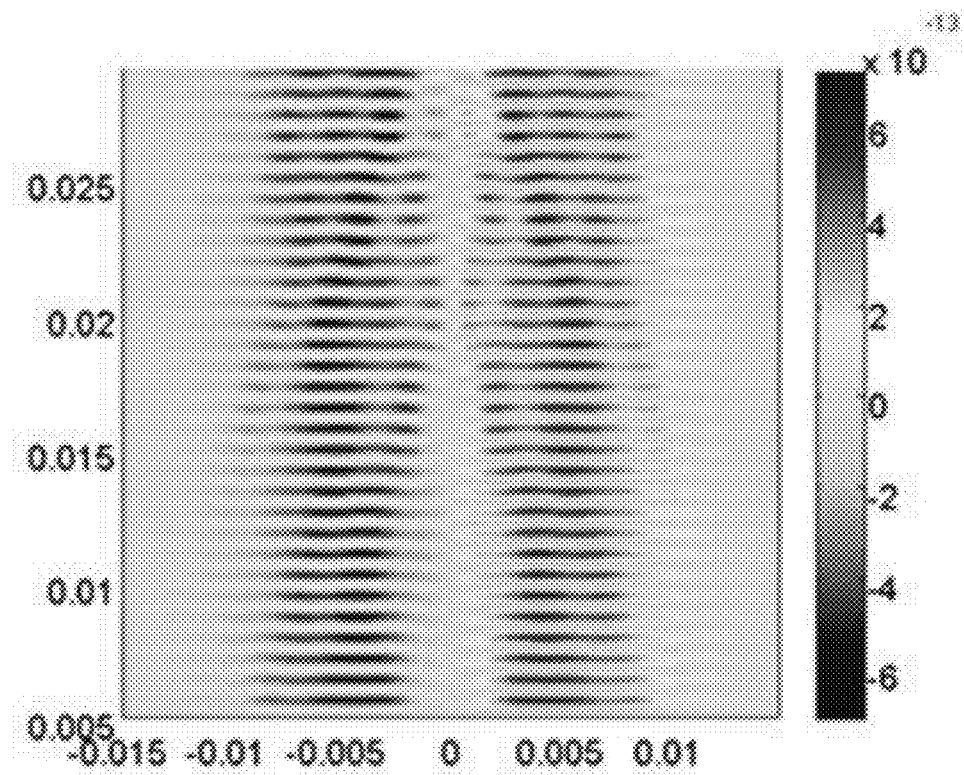
Figure 9C:
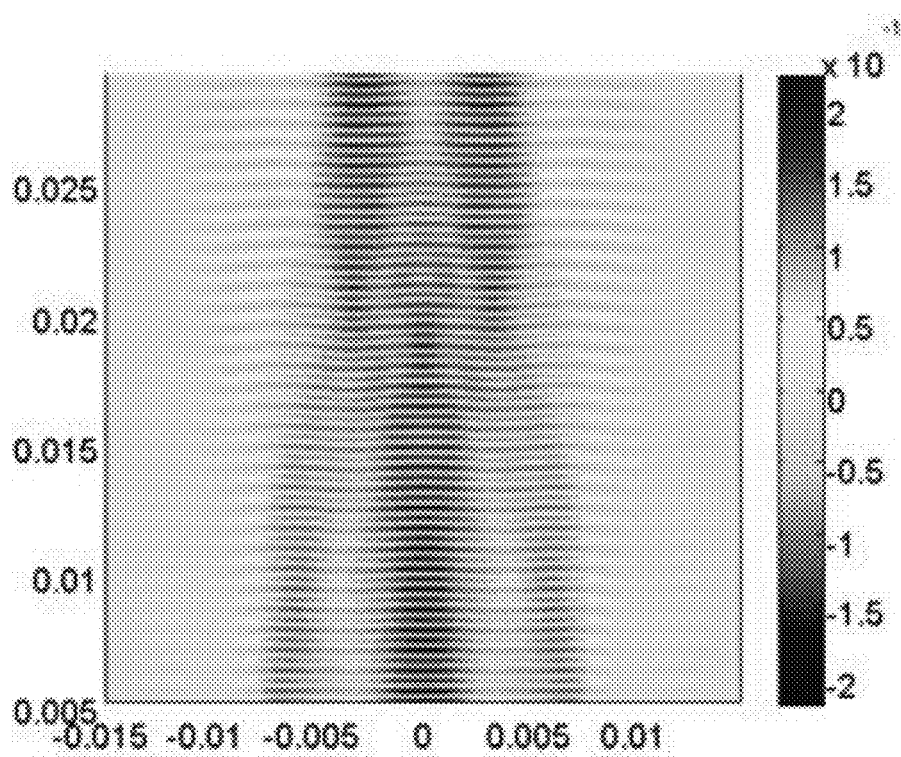
Figure 9D:
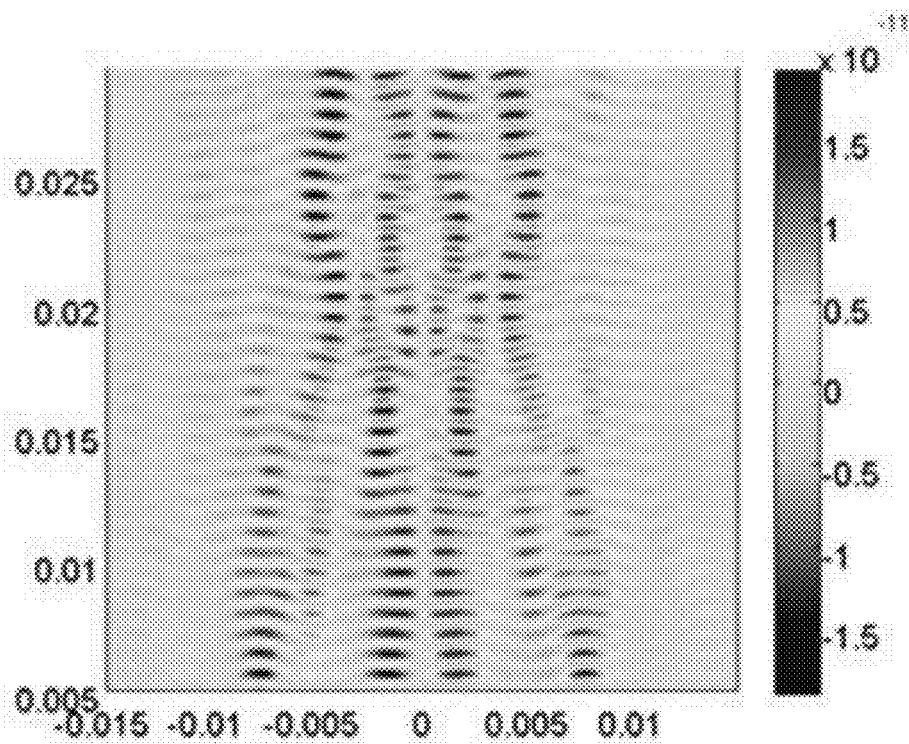

FIGS. 9A-9D show simulations of the difference in trapping pressure gradients between a single acoustic wave and a multimode acoustic wave. FIG. 9A shows the axial force associated with a single standing acoustic wave. FIG. 9B shows the lateral force due to a single standing acoustic wave. FIGS. 9C and 9D show the axial force and lateral force, respectively, in a multi-mode (higher order vibration modes having multiple nodes) piezoelectric crystal excitation where multiple standing waves are formed. The electrical input is the same as the single mode of FIGS. 9A and 9B, but the trapping force (lateral force) is 70 times greater (note the scale to the right in FIG. 9B compared to 9D). The figures were generated by a computer modeling simulation of a 1 MHz piezo-electric transducer driven by 10 V AC potted in an aluminum top plate in an open water channel terminated by a steel reflector (see FIG. 8). The field in FIGS. 9A and 9B is 960 kHz with a peak pressure of 400 kPa. The field in FIGS. 9C and 9D is 961 kHz with a peak pressure of 1400 kPa. In addition to higher forces, the 961 kHz field (FIGS. 9C and D) has more gradients and focal spots.

Figure 10:
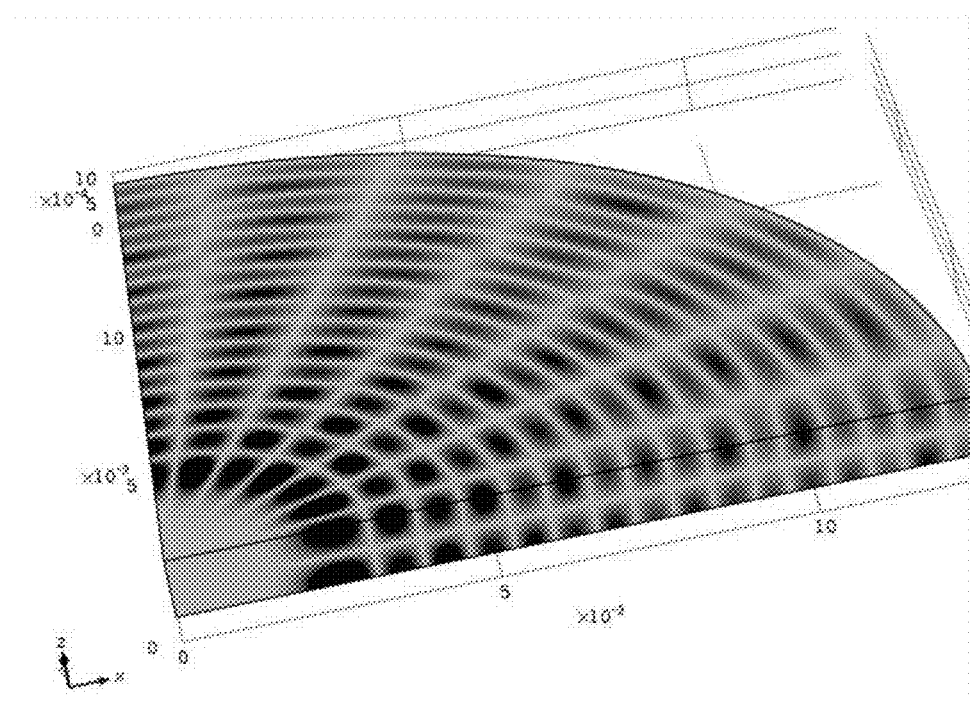
FIG. 10 is a picture of a simulated crystal showing the mode shape displacement in a crystal. The text for the x-axis reads ×10⁻³". The text for the z-axis includes "×10⁻³" and "×10⁻⁴".

FIG. 10 shows a three dimensional computer generated model of a mode shape calculation showing the out-of-plane displacement for a circular crystal driven at a frequency of 1 MHz.

FIGS. 11-17 are based on the model of FIG. 8 with a PZT-8 piezo-electric transducer operating at 2 MHz. The transducer is 1" wide and 0.04" thick, potted in an aluminum top plate (0.125" thick) in a 4"×2" water channel terminated by a steel reflector plate (0.180" thick). The acoustic beam spans a distance of 2". The depth dimension, which is 1", is not included in the 2D model. The transducer is driven at 15V and a frequency sweep calculation is done to identify the various acoustic resonances. The results of the three consecutive acoustic resonance frequencies, i.e., 1.9964 MHz (FIGS. 11, 12, and 13), 2.0106 MHz (FIGS. 14 and 15), and 2.025 MHz (FIGS. 16 and 17), are shown. The acoustic radiation force is calculated for an oil droplet with a radius of 5 micron, a density of 880 kg/m³, and speed of sound of 1700 m/sec. Water is the main fluid with a density of 1000 kg/m³, speed of sound of 1500 m/sec, and dynamic viscosity of 0.001 kg/msec. FIG. 11 shows the lateral (horizontal) acoustic radiation force. FIG. 12 shows the axial (vertical) component for a resonance frequency of 1.9964 MHz. FIG. 13 shows the acoustic pressure amplitude.

FIGS. 11-15 show relatively low lateral trapping forces. FIGS. 16-17 show that the relative magnitude of the lateral and axial component of the radiation force are very similar, indicating that it is possible to create large trapping forces, where the lateral force component is of similar magnitude or higher than the axial component. This is a new result and contradicts typical results mentioned in the literature.

A second result is that the acoustic trapping force magnitude exceeds that of the fluid drag force, for typical flow velocities on the order of mm/s, and it is therefore possible to use this acoustic field to trap the oil droplet. Of course, trapping at higher flow velocities can be obtained by increasing the applied power to the transducer. That is, the acoustic pressure is proportional to the driving voltage of the transducer. The electrical power is proportional to the square of the voltage.

A third result is that at the frequency shown, high trapping forces associated with this particular trapping mode extend across the entire flow channel, thereby enabling capture of oil droplets across the entire channel width. Finally, a comparison of the minima of the acoustic trapping force field, i.e., the locations of the trapped particles, with the observed trapping locations of droplets in the standing wave shows good agreement, indicating that modeling is indeed an accurate tool for the prediction of the acoustic trapping of particles. This will be shown in more detail below.

FIG. 14 shows the lateral acoustic radiation force component at a resonance frequency of 2.0106 MHz, and FIG. 15 shows the axial acoustic radiation force component at a resonance frequency of 2.0106 MHz. FIGS. 14 and 15 exhibit higher peak trapping forces than FIGS. 11 and 12. The lateral acoustic radiation forces exceed the axial radiation force. However, the higher trapping forces are located in the upper part of the flow channel, and do not span the entire depth of the flow channel. It would therefore represent a mode that is effective at trapping particles in the upper portion of the channel, but not necessarily across the entire channel. Again, a comparison with measured trapping patterns indicates the existence of such modes and trapping patterns.

FIG. 16 shows the lateral force component at a resonance frequency of 2.025 MHz, and FIG. 17 shows the axial acoustic radiation force component at a resonance frequency of 2.025 MHz. The acoustic field changes drastically at each acoustic resonance frequency, and therefore careful tuning of the system is critical. At a minimum, 2D models are necessary for accurate prediction of the acoustic trapping forces.

2D axisymmetric models were developed to calculate the trapping forces for circular transducers. The models were used to predict acoustic trapping forces on particles, which can then be used to predict particle trajectories in combination with the action of fluid drag and buoyancy forces. The models clearly show that it is possible to generate lateral acoustic trapping forces necessary to trap particles and overcome the effects of buoyancy and fluid drag. The models also show that circular transducers do not provide for large trapping forces across the entire volume of the standing wave created by the transducer, indicating that circular transducers only yield high trapping forces near the center of the ultrasonic standing wave generated by the transducer, but provide much smaller trapping forces toward the edges of the standing wave. This further indicates that the circular transducer only provides limited trapping for a small section of the fluid flow that would flow across the standing wave of the circular transducer, and no trapping near the edges of the standing wave.

FIG. 18 is a lin-log graph (linear y-axis, logarithmic x-axis) that shows the scaling of the acoustic radiation force, fluid drag force, and buoyancy force with particle radius. Calculations are done for a typical SAE-30 oil droplet used in experiments. The buoyancy force is a particle volume dependent force, and is therefore negligible for particle sizes on the order of micron, but grows, and becomes significant for particle sizes on the order of hundreds of microns. The fluid drag force scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain critical particle size. For further increases of particle size, the radiation force increases again in magnitude but with opposite phase (not shown in the graph). This pattern repeats for increasing particle sizes.

Initially, when a suspension is flowing through the system with primarily small micron sized particles, it is necessary for the acoustic radiation force to balance the combined effect of fluid drag force and buoyancy force for a particle to be trapped in the standing wave. In FIG. 18 this happens for a particle size of about 3.5 micron, labeled as $R_{c1}$. The graph then indicates that all larger particles will be trapped as well. Therefore, when small particles are trapped in the standing wave, particles coalescence/clumping/aggregation/agglomeration takes place, resulting in continuous growth of effective particle size. As the particle size grows, the acoustic radiation force reflects off the particle, such that large particles will cause the acoustic radiation force to decrease. Particle size growth continues until the buoyancy force becomes dominant, which is indicated by a second critical particle size, $R_{c2}$, at which size the particles will rise or sink, depending on their relative density with respect to the host fluid. As the particles rise or sink, they no longer reflect the acoustic radiation force, so that the acoustic radiation force then increases. Not all particles will drop out, and those remaining particles will continue to grow in size as well. This phenomenon explains the quick drops and rises in the acoustic radiation force beyond size $R_{c2}$. Thus, FIG. 18 explains how small particles can be trapped continuously in a standing wave, grow into larger particles or clumps, and then eventually will rise or settle out because of increased buoyancy force.

Because the circular transducers do not provide for large trapping forces across the entire volume, the effect of transducer shape on oil separation efficiency was investigated. A 1"-diameter circular PZT-8 crystal (FIG. 19, 110) and a 1"×1" square crystal (FIG. 19, 112) were used. Otherwise the experiment was run at identical conditions. Table 1 shows the results.

TABLE 1

Results of Investigation of Round and Square Transducer Shape

| Transducer Shape | Total Power Input (Watts) | Flow rate (ml/min) | Duration (min) | Capture Efficiency (%) |
|---|---|---|---|---|
| Round | 20 | 500 | 30 | 59% |
| Square | 20 | 500 | 30 | 91% |

The results indicate that the square transducer 112 provides better oil separation efficiencies than the round transducer 110, explained by the fact that the square transducer 112 provides better coverage of the flow channel with acoustic trapping forces, and that the round transducer only provides strong trapping forces along the centerline of the standing wave, confirming the findings of the numerical simulations.

The size, shape, and thickness of the transducer determine the transducer displacement at different frequencies of excitation, which in turn affects oil separation efficiency. Typically, the transducer is operated at frequencies near the thickness resonance frequency (half wavelength). Gradients in transducer displacement typically result in more places for oil to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

FIG. 20 shows the measured electrical impedance amplitude of the transducer as a function of frequency in the vicinity of the 2.2 MHz transducer resonance. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

To investigate the effect of the transducer displacement profile on acoustic trapping force and oil separation efficiencies, an experiment was repeated ten times, with all conditions identical except for the excitation frequency. Ten consecutive acoustic resonance frequencies, indicated by circled numbers 1-9 and letter A on FIG. 20, were used as excitation frequencies. The conditions were experiment duration of 30 min, a 1000 ppm oil concentration of approximately 5-micron SAE-30 oil droplets, a flow rate of 500 ml/min, and an applied power of 20 W.

As the emulsion passed by the transducer, the trapping lines of oil droplets were observed and characterized. The characterization involved the observation and pattern of the number of trapping lines across the fluid channel, as shown in FIG. 21A, for seven of the ten resonance frequencies identified in FIG. 20.

FIG. 21B shows an isometric view of the system in which the trapping line locations are being determined. FIG. 21C is a view of the system as it appears when looking down the inlet, along arrow 114. FIG. 21D is a view of the system as it appears when looking directly at the transducer face, along arrow 116.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. These experimentally observed results confirm the results expected from the differences when FIGS. 9A and 9B are compared to FIGS. 9C and 9D. Different displacement profiles of the transducer can produce different (more) trapping lines in the standing waves, with more gradients in displacement profile generally creating higher trapping forces and more trapping lines.

Table 2 summarizes the findings from an oil trapping experiment using a system similar to FIG. 27A. An important conclusion is that the oil separation efficiency of the acoustic separator is directly related to the mode shape of the transducer. Higher order displacement profiles generate larger acoustic trapping forces and more trapping lines resulting in better efficiencies. A second conclusion, useful for scaling studies, is that the tests indicate that capturing 5 micron oil droplets at 500 ml/min requires 10 Watts of power per square-inch of transducer area per 1" of acoustic beam span. The main dissipation is that of thermo-viscous absorption in the bulk volume of the acoustic standing wave. The cost of energy associated with this flow rate is 0.667 kWh per cubic meter.

TABLE 2

Trapping Pattern Capture Efficiency Study

| Resonance Peak Location | Total Power Input (Watts) | # of Trapping Lines | Flow rate (ml/min) | Duration (min) | Capture Efficiency (%) |
|---|---|---|---|---|---|
| 4 | 20 | 9 | 500 | 30 | 91% |
| 8 | 20 | 5 | 500 | 30 | 58% |
| A | 20 | 4 | 500 | 30 | 58% |
| 9 | 20 | 2 | 500 | 30 | 37% |

FIGS. 22 and 23 show photos of the trapped oil droplets in the nine trapping line pattern. Dashed lines are superimposed over the trapping lines. FIG. 24 shows the pressure field that matches the 9 trapping line pattern. The numerical model is a two-dimensional model; and therefore only three trapping lines are observed. Two more sets of three trapping lines exist in the third dimension perpendicular to the plane of the 2D model of FIG. 22 and FIG. 23. This comparison indicates that the numerical model is accurate in predicting the nature of the ultrasonic standing wave and the resulting trapping forces, again confirming the results expected from the differences when FIGS. 9A and 9B are compared to FIGS. 9C and 9D.

In larger systems, different transducer arrangements are feasible. FIG. 25 shows a transducer array 120 including three square 1"×1" crystals 120a, 120b, 120c. Two squares are parallel to each other, and the third square is offset to form a triangular pattern and get 100% acoustic coverage. FIG. 26 shows a transducer array 122 including two rectangular 1"×2.5" crystals 122a, 122b arranged with their long axes parallel to each other. Power dissipation per transducer was 10 W per 1"×1" transducer cross-sectional area and per inch of acoustic standing wave span in order to get sufficient acoustic trapping forces. For a 4" span of an intermediate scale system, each 1"×1" square transducer consumes 40 W. The larger 1"×2.5" rectangular transducer uses 100 W in an intermediate scale system. The array of three 1"×1" square transducers would consume a total of 120 W and the array of two 1"×2.5" transducers would consume about 200 W. Arrays of closely spaced transducers represent alternate potential embodiments of the technology. Transducer size, shape, number, and location can be varied as desired to generate desired three-dimensional acoustic standing waves.

A 4" by 2.5" flow cross sectional area intermediate scale apparatus 124 for separating a host fluid from a buoyant fluid or particulate is shown in FIG. 27A. The acoustic path length is 4". The apparatus is shown here in an orientation where the flow direction is downwards, which is used for separating less-dense particles from the host fluid. However, the apparatus may be essentially turned upside down to allow separation of particles which are heavier than the host fluid. Instead of a buoyant force in an upward direction, the weight of the agglomerated particles due to gravity pulls them downward. It should be noted that this embodiment is depicted as having an orientation in which fluid flows vertically. However, it is also contemplated that fluid flow may be in a horizontal direction, or at an angle.

A particle-containing fluid enters the apparatus through inlets 126 into an annular plenum 131. The annular plenum has an annular inner diameter and an annular outer diameter. Two inlets are visible in this illustration, though it is contemplated that any number of inlets may be provided as desired. In particular embodiments, four inlets are used. The inlets are radially opposed and oriented.

A contoured nozzle wall 129 reduces the outer diameter of the flow path in a manner that generates higher velocities near the wall region and reduces turbulence, producing near plug flow as the fluid velocity profile develops, i.e. the fluid is accelerated downward in the direction of the centerline with little to no circumferential motion component and low flow turbulence. This generates a chamber flow profile that is optimum for acoustic separation and particle collection. The fluid passes through connecting duct 127 and into a flow/separation chamber 128. As seen in the zoomed-in contoured nozzle 129 in FIG. 27B, the nozzle wall also adds a radial motion component to the suspended particles, moving the particles closer to the centerline of the apparatus and generating more collisions with rising, buoyant agglomerated particles. This radial motion will allow for optimum scrubbing of the particles from the fluid in the connecting duct 127 prior to reaching the separation chamber. The contoured nozzle wall 129 directs the fluid in a manner that generates large scale vortices at the entrance of the collection duct 133 to also enhance particle collection. Generally, the flow area of the device 124 is designed to be continually decreasing from the annular plenum 131 to the separation chamber 128 to assure low turbulence and eddy formation for better particle separation, agglomeration, and collection. The nozzle wall has a wide end and a narrow end. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension.

Returning to FIG. 27A, the flow/separation chamber 128 includes a transducer array 130 and reflector 132 on opposite sides of the chamber. In use, standing waves 134 are created between the transducer array 130 and reflector 132. These standing waves can be used to agglomerate particles, and this orientation is used to agglomerate particles that are buoyant (e.g. oil). Fluid, containing residual particles, then exits through flow outlet 135.

As the buoyant particles agglomerate, they eventually overcome the combined effect of the fluid flow drag forces and acoustic radiation force, and their buoyant force 136 is sufficient to cause the buoyant particles to rise upwards. In this regard, a collection duct 133 is surrounded by the annular plenum 131. The larger particles will pass through this duct and into a collection chamber 140. This collection chamber can also be part of an outlet duct. The collection duct and the flow outlet are on opposite ends of the apparatus.

It should be noted that the buoyant particles formed in the separation chamber 128 subsequently pass through the connecting duct 127 and the nozzle wall 129. This causes the incoming flow from the annular plenum to flow over the rising agglomerated particles due to the inward radial motion imparted by the nozzle wall. This allows the rising particles to also trap smaller particles in the incoming flow, increasing scrubbing effectiveness. The length of the connecting duct 127 and the contoured nozzle wall 129 thus increase scrubbing effectiveness. Especially high effectiveness is found for particles with a size of 0.1 microns to 20 microns, where efficiency is very low for conventional methods.

The design here provides an optimized velocity profile with low flow turbulence at the inlet to the flow chamber 128, a scrubbing length before the flow chamber to enhance particle agglomeration and/or coalescence before acoustic separation, and the use of the collection vortices to aid particle removal at the collection duct 133.

In experiments carried out with the apparatus of FIG. 27A, transducer array 120 was installed in system 124, removed, and then transducer array 122 installed. The arrays were operated in parallel such that each transducer was driven by the same voltage signal from the amplifier. The electronic drive circuit consisted of a function generator and a 300 W A300 ENI RF amplifier. The results of the testing are shown in Table 3. The first test used only the two of the 1"×1" square transducers or array 120, oriented parallel to each other, and was run at a flow rate of 1300 ml/min. It resulted in an oil separation efficiency of 88%. The next test involved all three square transducers and a flow rate of 2000 ml/min, and yielded an efficiency of 93%. These results are excellent and demonstrate that the technology is scalable to larger flow channels driven by arrays of transducers. The next set of tests involved the 1"×2.5" rectangular transducer array 122. For the first test, only one transducer was run and yielded an efficiency of 87%. The second test with both transducers operating yielded an efficiency of 97%. For the 1"×2.5" transducers, the power level that was used was based on operating the transducer at safe levels. For these tests, the cost of energy for the intermediate system is 1 kWh per cubic meter.

TABLE 3

Intermediate System Test Results

| Transducer Configuration | Number of Transducers Active | Total Power Input (Watts) | Flow rate (ml/min) | Duration (min) | Capture Efficiency (%) |
|---|---|---|---|---|---|
| 1" × 1" Transducers | 2 | 80 | 1300 | 15 | 88% |
| 1" × 1" Transducers | 3 | 120 | 2000 | 15 | 93% |
| 1" × 2.5" Transducers | 1 | 100 | 2000 | 8 | 87% |
| 1" × 2.5" Transducers | 2 | 100 | 1000 | 15 | 97% |

Numerical modeling was also done for the intermediate sized system with a span of 4" for the acoustic standing wave.

Multiple transducers were modeled to investigate the coupling effect between transducers. Frequency sweeps were performed and the resonance frequencies for which the acoustic mode shapes couple strongly to the higher order mode shapes of the transducer were identified. The comparisons between numerical and experimental results are excellent and demonstrate the accuracy of the models. FIG. 28 shows the acoustic pressure field of a model with two transducers on the right side. A photograph of the trapped oil droplets in the standing wave is shown in FIG. 29. Both experiment and model show identical features. At certain excitation frequencies, oil droplets were trapped in the standing wave well outside the fluid volume defined by the transducer area, indicating an expanded acoustic field with strong trapping forces. FIG. 30 shows a photograph of such trapped oil droplets. FIG. 31 shows an acoustic pressure field model which predicts identical features.

The transducer is typically a thin piezoelectric plate, which is operated in the (3,3) mode, with electric field in the z-axis and primary displacement in the z-axis, as shown in FIGS. 38A-38D. The transducer is typically coupled on one side by air (i.e. the air gap within the transducer) and on the other side by water (i.e. the host fluid). The types of waves generated in the plate are known as composite waves. A subset of composite waves in the piezoelectric plate is similar to leaky symmetric (also referred to as compressional or extensional) Lamb waves. The piezoelectric nature of the plate typically results in the excitation of symmetric Lamb waves. The waves are leaky because they radiate into the water layer, which result in the generation of the acoustic standing waves in the water layer. Symmetric Lamb waves have displacement profiles that are symmetric with respect to the neutral axis of the plate, as is shown on the left-hand side of FIG. 32. Symmetric Lamb waves seem to be more desirable that anti-symmetric Lamb waves, as is shown on the right hand side of FIG. 32. Lamb waves exist in thin plates of infinite extent with stress free conditions on its surfaces. Because the transducers of this embodiment are finite in nature the actual modal displacements are more complicated. FIG. 33 shows the typical variation of the in-plane displacement (x-displacement) and out-of-plane displacement (y-displacement) across the thickness of the plate, the in-plane displacement being an even function across the thickness of the plate and the out-of-plane displacement being an odd function. Because of the finite size of the plate, the displacement components vary across the width and length of the plate. An example is shown in FIGS. 38A-38D, which illustrate the (3,3) displacement mode. The out-of-plane component is characterized by three periodic undulations and the in-plane component by three oscillations. This displacement profile of the transducer is referred to as a (3,3) mode. Additional higher frequency oscillations are seen in the displacement profile, e.g., an oscillation with 25 peaks, which is the 25th harmonic of the fundamental longitudinal mode in the width and length direction, since the width and length to thickness ratio is 25 for the given transducer. In general, a (m, n) mode is a displacement mode of the transducer in which there are m undulations in transducer displacement in the width direction and n undulations in the length direction, and with the thickness variation as described in FIG. 33. The maximum number of m and n is a function of the dimension of the crystal and the frequency of excitation.

As previously discussed, the transducers are driven so that the piezoelectric crystal vibrates in higher order modes of the general formula (m, n), where m and n are independently 1 or greater. FIGS. 34A-38D show, in order, illustrations of vibration modes (1,1), (2,1), (1,2), (2,2), and (3,3) of a rectangular plate. In each figure, the plate 156 has a length 150 that is equal to or longer than its width 152. A perspective view, a view along the length (y=0), and a view along the width (x=0) are provided for each vibration mode.

FIG. 34A shows the vibration mode (1,1). In this mode, the plate has its maximal displacement at antinode 154 in the center of the rectangular plate 156. FIG. 34B shows the view along the length 150 (i.e. along arrow 151) and FIG. 34C shows the view along the width 152 (along arrow 153). FIG. 34D shows the in-plane displacement associated with vibration mode (1,1).

FIG. 35A shows mode (2,1). Here, there are two antinodes 160 (peaking above the plane of the membrane 156). These two antinodes are on opposite sides of a nodal line of minimal displacement 162 which runs parallel to width 152 and at the center of length 150. Note that in the case of a square transducer (one in which length 150 is equal to width 152, as in the transducer 112 of FIG. 19 and in FIG. 25), the (1,2) and (2,1) modes are mere rotations of each other. FIG. 35B shows the view along the length (i.e. along arrow 161) and FIG. 35C shows the view along the width (i.e. along arrow 163).

FIG. 36A shows mode (1,2). This mode also has two antinodes 166 and one nodal line 164. Compared to FIG. 35A, the difference here is that the nodal line 164 runs lengthwise (parallel to length 150) and at the center of width 152. FIG. 36B shows the view along arrow 165 and FIG. 36C shows the view along arrow 167.

FIG. 37A, showing the (2,2), mode, has four antinodes 174 and two nodal lines 170, 172. One nodal line 172 is in the center of width 152, parallel to length 150. The other nodal line 170 is in the center of length 150, parallel to width 152. FIG. 37B shows the view along arrow 171 and FIG. 37C shows the view along arrow 173.

FIG. 38A shows the vibration mode (3,3). There are two lengthwise nodal lines 186 and two width-wise nodal lines 180. Three sets of antinodes 182 are created by the nodal lines 180, and three sets of antinodes 184 are created by the nodal lines 186. This results in a total of nine antinodes resulting from their intersection in each direction. FIG. 38B shows the view along arrow 181 and FIG. 38C shows the view along arrow 183. FIG. 38D shows the in-plane displacement associated with vibration mode (3,3).

These modes are illustrative and, generally, the transducers will vibrate in higher order modes than (2,2). Higher order modes will produce more nodes and antinodes, result in three-dimensional standing waves in the water layer, characterized by strong gradients in the acoustic field in all directions, not only in the direction of the standing waves, but also in the lateral directions. As a consequence, the acoustic gradients result in stronger trapping forces in the lateral direction.

FIGS. 39A-39C show the pressure field generated by a transducer operating at different displacement modes. In each figure, the vibrating crystal is illustrated at y=1 inch, and the resultant standing wave that is transmitted into the fluid is illustrated below. FIG. 39A shows the magnitude of the acoustic pressure when the water layer is driven by a transducer operating predominantly at the (1,1) mode. The resulting pressure field is one that can be described as a primarily one-dimensional standing wave with a slowly varying acoustic pressure amplitude in the lateral direction. FIG. 39B shows the pressure field excited by a transducer operating predominantly at the (2,2) mode, and similarly FIG. 39C shows the pressure field when the transducer is operated predominantly at the (3,3) mode. We observe that a (2,2) excitation leads to the generation of four (2×2) parallel acoustic standing waves, and a (3,3) leads to nine (3×3) standing waves. The ratio of the lateral acoustic radiation force component to the axial component was calculated for these three pressure fields. Excitation at the (2,2) mode leads to the doubling of that ratio in comparison to the (1,1) mode. Excitation at the (3,3) mode leads to the tripling of the ratio of the (1,1) mode, hereby demonstrating the benefit of exciting higher order modes.

Generally speaking but with specific reference to the transducer array of FIG. 27A, the transducer setup of the present disclosure creates a three dimensional pressure field which includes standing waves perpendicular to the fluid flow. The pressure gradients are large enough to generate acoustophoretic forces orthogonal to the standing wave direction (i.e., the acoustophoretic forces are parallel to the fluid flow direction) which are of the same order of magnitude as the acoustophoretic forces in the wave direction. This permits enhanced particle trapping and collection in the flow chamber and along well-defined trapping lines, as opposed to merely trapping particles in collection planes as in conventional devices. The particles have significant time to move to nodes or anti-nodes of the standing waves, generating regions where the particles can concentrate, agglomerate, and/or coalesce.

In some embodiments, the fluid flow has a Reynolds number of up to 1500, i.e. laminar flow is occurring. For practical application in industry, the Reynolds number is usually from 10 to 1500 for the flow through the system. The particle movement relative to the fluid motion generates a Reynolds number much less than 1.0. The Reynolds number represents the ratio of inertial flow effects to viscous effects in a given flow field. For Reynolds numbers below 1.0, viscous forces are dominant in the flow field. This results in significant damping where shear forces are predominant throughout the flow. This flow where viscous forces are dominant is called Stokes flow, The flow of molasses is an example. Wall contouring and streamlining have very little importance.

It is associated with the flow of very viscous fluids or the flow in very tiny passages, like MEMS devices. Inlet contouring has little importance. The flow of the particles relative to the fluid in FSA particle separator will be Stokes flow because both the particle diameters and the relative velocities between the particles and fluid are very small. On the other hand, the Reynolds number for the flow through the system will be much greater than 1.0 because the fluid velocity and inlet diameter are much larger. For Reynolds numbers much greater than 1.0, viscous forces are dominant only where the flow is in contact with the surface. This viscous region near the surface is called a boundary layer and was first recognized by Ludwig Prandtl (Reference 2). In duct flow, the flow will be laminar if the Reynolds number is significantly above 1.0 and below 2300 for fully developed flow in the duct. The wall shear stress at the wall will diffuse into the stream with distance. At the inlet of the duct, flow velocity starts off uniform. As the flow moves down the duct, the effect of wall viscous forces will diffuse inward towards the centerline to generate a parabolic velocity profile. This parabolic profile will have a peak value that is twice the average velocity. The length required for the parabolic profile to develop is a function of the Reynolds number. For a Reynolds number of 20, which is typical for CHO operation, the development length will be 1.2 duct diameters. Thus, fully developed flow happens very quickly. This peak velocity in the center can be detrimental to acoustic particle separation. Also, at laminar flow Reynolds numbers turbulence, can occur and flow surface contouring is very important in controlling the flow. For these reasons, the separator was designed with an annular inlet plenum and collector tube The large annular plenum is followed by an inlet wall nozzle that accelerates and directs the fluid inward toward the centerline as shown in FIG. 27B. The wall contour will have a large effect on the profile. The area convergence increases the flow average velocity, but it is the wall contour that determines the velocity profile. The nozzle wall contour will be a flow streamline, and is designed with a small radius of curvature in the separator.

The transducer(s) is/are used to create a pressure field that generates forces of the same order of magnitude both orthogonal to the standing wave direction and in the standing wave direction. When the forces are roughly the same order of magnitude, particles of size 0.1 microns to 300 microns will be moved more effectively towards regions of agglomeration ("trapping lines"), as seen in FIG. 21C. Because of the equally large gradients in the orthogonal acoustophoretic force component, there are "hot spots" or particle collection regions that are not located in the regular locations in the standing wave direction between the transducer 130 and the reflector 132. Hot spots are located in the maxima or minima of acoustic radiation potential. Such hot spots represent particle collection locations which allow for better wave transmission between the transducer and the reflector during collection and stronger inter-particle forces, leading to faster and better particle agglomeration.

One application of the acoustophoretic separator is separation of cells from a medium, such as the separation of red blood cells, described in U.S. application Ser. No. 13/866,584 to Dutra and Lipkens, entitled "ACOUSTOPHORETIC SEPARATION OF LIPID PARTICLES FROM RED BLOOD CELLS," the entirety of which is hereby fully incorporated by reference.

Another application is the separation of a biological therapeutic protein from the biologic cells that produce the protein. In this regard, current methods of separation require filtration or centrifugation, either of which can damage cells, releasing protein debris and enzymes into the purification process and increasing the load on downstream portions of the purification system. It is desirable to be able to process volumes having higher cell densities, because this permits collection of larger amounts of the therapeutic protein and better cost efficiencies.

FIG. 40A and FIG. 40B are exploded views showing the various parts of acoustophoretic separators. FIG. 40A has only one separation chamber, while FIG. 40B has two separation chambers.

Referring to FIG. 40A, fluid enters the separator 190 through a four-port inlet 191. A transition piece 192 is provided to create plug flow through the separation chamber 193. A transducer 40 and a reflector 194 are located on opposite walls of the separation chamber. Fluid then exits the separation chamber 193 and the separator through outlet 195.

FIG. 40B has two separation chambers 193. A system coupler 196 is placed between the two chambers 193 to join them together.

Acoustophoretic separation has been tested on different lines of Chinese hamster ovary (CHO) cells. In one experiment, a solution with a starting cell density of $8.09 \times 10^6$ cells/mL, a turbidity of 1,232 NTU, and cell viability of roughly 75% was separated using a system as depicted in FIG. 40A. The transducers were 2 MHz crystals, run at approximately 2.23 MHz, drawing 24-28 Watts. A flow rate of 25 mL/min was used. The result of this experiment is shown in FIG. 41A.

In another experiment, a solution with a starting cell density of $8.09 \times 10^6$ cells/mL, a turbidity of 1,232 NTU, and cell viability of roughly 75% was separated. This CHO cell line had a bi-modal particle size distribution (at size 12 µm and 20 µm). The result is shown in FIG. 41B.

FIG. 41A and FIG. 41B were produced by a Beckman Coulter Cell Viability Analyzer. Other tests revealed that frequencies of 1 MHz and 3 MHz were not as efficient as 2 MHz at separating the cells from the fluid.

In other tests at a flow rate of 10 L/hr, 99% of cells were captured with a confirmed cell viability of more than 99%. Other tests at a flow rate of 50 mL/min (i.e. 3 L/hr) obtained a final cell density of $3 \times 10^6$ cells/mL with a viability of nearly 100% and little to no temperature rise. In yet other tests, a 95% reduction in turbidity was obtained at a flow rate of 6 L/hr.

Testing on the scaled unit shown in FIG. 27 was performed using yeast as a simulant for CHO for the biological applications. For these tests, at a flow rate of 15 L/hr, various frequencies were tested as well as power levels. Table 1 shows the results of the testing.

TABLE 1

| 2.5" × 4" System results at 15 L/hr Flow rate | | | |
|---|---|---|---|
| Frequency (MHz) | 30 Watts | 37 Watts | 45 Watts |
| 2.2211 | 93.9 | 81.4 | 84.0 |
| 2.2283 | 85.5 | 78.7 | 85.4 |
| 2.2356 | 89.1 | 85.8 | 81.0 |
| 2.243 | 86.7 | — | 79.6 |

In biological applications, many parts, e.g. the tubing leading to and from the housing, inlets, exit plenum, and entrance plenum, may all be disposable, with only the transducer and reflector to be cleaned for reuse. Avoiding centrifuges and filters allows better separation of the CHO cells without lowering the viability of the cells. The form factor of the acoustophoretic separator is also smaller than a filtering system, allowing the CHO separation to be miniaturized. The transducers may also be driven to create rapid pressure changes to prevent or clear blockages due to agglomeration of CHO cells. The frequency of the transducers may also be varied to obtain optimal effectiveness for a given power.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method for continuously separating a second fluid or a particulate from a host fluid, comprising:
   flowing a mixture of the host fluid and the second fluid or particulate through an apparatus, the apparatus comprising:
      a flow chamber having at least one inlet and at least one outlet;
      at least one ultrasonic transducer located on a wall of the flow chamber, the transducer including a piezoelectric material driven by a voltage signal to create a multi-dimensional standing wave in the flow chamber; and
      a reflector located on the wall on the opposite side of the flow chamber from the at least one ultrasonic transducer; and
   sending a voltage signal to drive the at least one ultrasonic transducer to create the multi-dimensional standing wave, such that the second fluid or particulate is continuously trapped in the standing wave, and then agglomerates, aggregates, clumps, or coalesces together, and subsequently rises or settles out of the host fluid due to buoyancy or gravity forces, and exits the flow chamber;
   wherein the multi-dimensional standing wave results in an acoustic radiation force having an axial force component and a lateral force component that are of the same order of magnitude; and
   wherein the ultrasonic transducer comprises:
      a housing having a top end, a bottom end, and an interior volume; and
      a crystal at the bottom end of the housing having an exposed exterior surface and an interior surface, the crystal being able to vibrate when driven by a voltage signal.

2. The method of claim 1, wherein the particulate is Chinese hamster ovary (CHO) cells, NS0 hybridoma cells, baby hamster kidney (BHK) cells, or human cells.

3. The method of claim 1, wherein greater than 90% of the particulate is separated from the host fluid on a volume basis.

4. The method of claim 1, wherein a backing layer contacts the interior surface of the crystal, the backing layer being made of a substantially acoustically transparent material.

5. The method of claim 4, wherein the substantially acoustically transparent material is balsa wood, cork, or foam.

6. The method of claim 4, wherein the substantially acoustically transparent material has a thickness of up to 1 inch.

7. The method of claim 4, wherein the substantially acoustically transparent material is in the form of a lattice.

8. The method of claim 1, wherein an exterior surface of the crystal is covered by a wear surface material with a thickness of a half wavelength or less, the wear surface material being a urethane, epoxy, or silicone coating.

9. The method of claim 1, wherein the crystal has no backing layer or wear layer.

10. The method of claim 1, wherein the multi-dimensional standing wave traps particles in a low field having a linear velocity of from 0.1 millimeter/second to greater than 1 centimeter/second.

11. The method of claim 1, wherein the piezoelectric material vibrates in a higher order mode shape.

12. The method of claim 1, wherein the piezoelectric material vibrates to create a displacement profile having multiple maxima and minima.

13. The method of claim 1, wherein the mixture flows vertically downwards, and the second fluid or particulate floats upward to a collection duct.

14. The method of claim 1, wherein the mixture flows vertically upwards, and the second fluid or particulate sinks down to a collection duct.

15. The method of claim 1, wherein the standing waves are normal to the vertical flow direction.

16. The method of claim 1, wherein hot spots are generated that are located at a minimum of the acoustic radiation potential.

17. The method of claim 1, wherein the voltage signal has a sinusoidal, square, sawtooth, triangle, or pulsed waveform.

18. The method of claim 1, wherein the voltage signal has a frequency of 100 kHz to 10 MHz.

19. The method of claim 1, wherein the voltage signal is driven with amplitude or frequency modulation start/stop capability to eliminate acoustic streaming.

20. The method of claim 1, wherein the mixture of the host fluid and the second fluid or particulate has a Reynolds number of 1500 or less prior to entering the flow chamber.

21. The method of claim 1, wherein the particulate has a size of from about 0.1 microns to about 300 microns.

22. The method of claim 1, wherein the mixture of the host fluid and the second fluid or particulate flows through the flow chamber at a rate of at least 0.25 liters/hour.

23. A method of continuously separating a second fluid or a particulate from a host fluid, comprising:
- flowing a mixture of the host fluid and the second fluid or particulate through an apparatus, the apparatus comprising:
  - a flow chamber having at least one inlet and at least one outlet;
  - at least one ultrasonic transducer located on a wall of the flow chamber, the transducer including a piezoelectric material driven by a voltage signal to create a multi-dimensional standing wave in the flow chamber; and
  - a reflector located on the wall on the opposite side of the flow chamber from the at least one ultrasonic transducer; and
- sending a voltage signal to drive the at least one ultrasonic transducer to separate the second fluid or particulate from the host fluid;
- wherein the multi-dimensional standing wave results in an acoustic radiation force having an axial force component and a lateral force component that are of the same order of magnitude; and
- wherein the mixture flows from an apparatus inlet through an annular plenum and past a contoured nozzle wall prior to entering the flow chamber inlet.

24. The method of claim 23, wherein the separated second fluid or particulate agglomerates, aggregates, clumps, or coalesces and then rises, and wherein the inflowing mixture is directed to flow past the rising second fluid or particulate by the contoured nozzle wall.

25. The method of claim 23, wherein the mixture flows from the apparatus inlet through the annular plenum and past the contoured nozzle wall to generate large scale vortices at the entrance to a collection duct prior to entering the flow chamber inlet, thus enhancing separation of the second fluid or particulate from the host fluid.

26. The method of claim 23, wherein the reflector has a non-planar surface.

27. The method of claim 23, wherein the apparatus further comprises:
- the apparatus inlet that leads to the annular plenum;
- the contoured nozzle wall downstream of the apparatus inlet;
- a collection duct surrounded by the annular plenum; and
- a connecting duct joining the contoured nozzle wall to the flow chamber inlet.

28. The method of claim 23, wherein the at least one outlet includes a first outlet whose output substantially comprises the host fluid containing expressed biomolecules and a second outlet whose output substantially comprises the second fluid or particulate that has been separated from the mixture, wherein the particulate is Chinese hamster ovary (CHO) cells, NS0 hybridoma cells, baby hamster kidney (BHK) cells, or human cells.

29. A method for continuously separating a second fluid or a particulate from a host fluid, comprising:
- flowing a mixture of the host fluid and the second fluid or particulate through an apparatus, the apparatus comprising:
  - a flow chamber having at least one inlet and at least one outlet;
  - a contoured nozzle wall upstream of the flow chamber inlet;
  - at least one ultrasonic transducer located on a wall of the flow chamber, the transducer including a piezoelectric material driven by a voltage signal to create a multi-dimensional standing wave in the flow chamber; and
  - a reflector located on the wall on the opposite side of the flow chamber from the at least one ultrasonic transducer; and
- sending a voltage signal to the at least one ultrasonic transducer to create the multi-dimensional standing wave, such that the second fluid or particulate is continuously trapped in the standing wave, and then agglomerates, aggregates, clusters, or coalesces together, and subsequently rises or settles out of the host fluid due to buoyancy or gravity forces;
- wherein the multi-dimensional standing wave results in an acoustic radiation force having an axial force component and a lateral force component that are of the same order of magnitude.

30. The method of claim 23, wherein the particulate is Chinese hamster ovary (CHO) cells, NS0 hybridoma cells, baby hamster kidney (BHK) cells, or human cells.

31. The method of claim 23, wherein greater than 90% of the particulate is separated from the host fluid on a volume basis.

32. The method of claim 29, wherein the particulate is Chinese hamster ovary (CHO) cells, NS0 hybridoma cells, baby hamster kidney (BHK) cells, or human cells.

33. The method of claim 29, wherein greater than 90% of the particulate is separated from the host fluid on a volume basis.

34. The method of claim 29, wherein the ultrasonic transducer comprises:
- a housing having a top end, a bottom end, and an interior volume; and
- a crystal at the bottom end of the housing having an exposed exterior surface and an interior surface, the crystal being able to vibrate when driven by a voltage signal.

35. The method of claim 34, wherein a backing layer contacts the interior surface of the crystal, the backing layer being made of a substantially acoustically transparent material.

36. The method of claim 35, wherein the substantially acoustically transparent material is balsa wood, cork, or foam.

37. The method of claim 35, wherein the substantially acoustically transparent material has a thickness of up to 1 inch.

38. The method of claim 35, wherein the substantially acoustically transparent material is in the form of a lattice.

39. The method of claim 34, wherein an exterior surface of the crystal is covered by a wear surface material with a thickness of a half wavelength or less, the wear surface material being a urethane, epoxy, or silicone coating.

40. The method of claim 34, wherein the crystal has no backing layer or wear layer.

41. The method of claim 29, wherein the multi-dimensional standing wave traps particles in a low field having a linear velocity of from 0.1 millimeter/second to greater than 1 centimeter/second.

42. The method of claim 29, wherein the piezoelectric material vibrates in a higher order mode shape.

43. The method of claim 29, wherein the piezoelectric material vibrates to create a displacement profile having multiple maxima and minima.

44. The method of claim 29, wherein the mixture flows vertically downwards, and the second fluid or particulate floats upward to a collection duct.

45. The method of claim 29, wherein the mixture flows vertically upwards, and the second fluid or particulate sinks down to a collection duct.

46. The method of claim 29, wherein the standing waves are normal to the vertical flow direction.

47. The method of claim 29, wherein hot spots are generated that are located at a minimum of the acoustic radiation potential.

48. The method of claim 29, wherein the voltage signal has a sinusoidal, square, sawtooth, triangle, or pulsed waveform.

49. The method of claim 29, wherein the voltage signal has a frequency of 100 kHz to 10 MHz.

50. The method of claim 29, wherein the voltage signal is driven with amplitude or frequency modulation start/stop capability to eliminate acoustic streaming.

51. The method of claim 29, wherein the mixture of the host fluid and the second fluid or particulate has a Reynolds number of 1500 or less prior to entering the flow chamber.

52. The method of claim 29, wherein the particulate has a size of from about 0.1 microns to about 300 microns.

53. The method of claim 29, wherein the mixture of the host fluid and the second fluid or particulate flows through the flow chamber at a rate of at least 0.25 liters/hour.

54. The method of claim 29, wherein the reflector has a non-planar surface.

* * * * *